United States Patent [19]
Klieman et al.

[11] Patent Number: 5,827,323
[45] Date of Patent: Oct. 27, 1998

[54] SURGICAL INSTRUMENT FOR ENDOSCOPIC AND GENERAL SURGERY

[75] Inventors: Charles H. Klieman, 21 Lochmoor La., Newport Beach, Calif. 92660; John M. Stiggelbout, Sausalito, Calif.

[73] Assignee: Charles H. Klieman, Whittier, Calif.

[21] Appl. No.: 729,683

[22] Filed: Oct. 4, 1996

Related U.S. Application Data

[63] Continuation-in-part of Ser. No. 471,988, Jun. 6, 1995, which is a continuation-in-part of Ser. No. 295,352, Aug. 24, 1994, abandoned, which is a continuation of Ser. No. 95,739, Jul. 21, 1993, abandoned.

[51] Int. Cl.$^6$ ..................................... A61B 17/28
[52] U.S. Cl. ............................... 606/205; 606/170
[58] Field of Search .................. 606/205–208, 606/174, 170, 51, 52; 128/751; 600/564

[56] References Cited

U.S. PATENT DOCUMENTS

| | | |
|---|---|---|
| 3,730,185 | 5/1973 | Cook et al. . |
| 3,888,004 | 6/1975 | Coleman . |
| 4,258,716 | 3/1981 | Sutherland . |
| 4,320,761 | 3/1982 | Haddad . |
| 4,672,964 | 6/1987 | Dee et al. . |
| 4,688,555 | 8/1987 | Wardle . |
| 4,763,669 | 8/1988 | Jaeger . |
| 4,838,853 | 6/1989 | Parisi . |
| 4,861,332 | 8/1989 | Parisi . |
| 4,872,456 | 10/1989 | Hasson . |
| 4,877,026 | 10/1989 | de Laforcade . |
| 4,880,015 | 11/1989 | Nierman . |
| 4,940,468 | 7/1990 | Petillo . |
| 4,978,333 | 12/1990 | Broadwin et al. . |
| 4,986,825 | 1/1991 | Bays et al. . |
| 5,024,652 | 6/1991 | Dumenek et al. . |
| 5,026,387 | 6/1991 | Thomas . |
| 5,112,299 | 5/1992 | Pascaloff . |
| 5,133,736 | 7/1992 | Bales, Jr. et al. . |
| 5,174,300 | 12/1992 | Bales et al. . |
| 5,176,697 | 1/1993 | Hasson et al. . |
| 5,209,747 | 5/1993 | Knoepfler . |
| 5,224,954 | 7/1993 | Watts et al. . |
| 5,254,130 | 10/1993 | Poncet et al. . |
| 5,258,007 | 11/1993 | Spetzler et al. . |

(List continued on next page.)

FOREIGN PATENT DOCUMENTS

| | | |
|---|---|---|
| 0 577 423 A2 | 1/1994 | European Pat. Off. . |
| 2681775-A1 | 4/1993 | France . |
| 43 00 307 A1 | 7/1994 | Germany . |
| 43 07 539 A1 | 9/1994 | Germany . |
| 980703-A | 12/1982 | U.S.S.R. . |
| WO 91/02493 | 3/1991 | WIPO . |
| WO 93/07816 | 4/1993 | WIPO . |
| WO 94/20034 | 9/1994 | WIPO . |

OTHER PUBLICATIONS

Hospital Price List, effective Feb. 24, 1992, published by Ethicon, a Johnson & Johnson Company.
Advertisement dated May of 1992 for Auto–Sector TM published by Omni–Tract Surgical.

*Primary Examiner*—Michael H. Thaler
*Attorney, Agent, or Firm*—Fish & Richardson P.C., P.A.

[57] ABSTRACT

An endoscopic surgical instrument with manual controls and single-handed design has a tubular barrel with a handle at its proximal end and an end effector at its distal end. A linkage extends through the tubular barrel and connects the handle with the end effector. The handle has a stationary finger loop, in fixed alignment with the longitudinal axis of the tubular barrel, and is designed to receive a middle finger. The handle also includes a thumb lever, a fingerwheel control and a rotate control. The thumb lever, operated by the thumb of the hand gripping the finger loop, actuates the end effector; the fingerwheel control, operated by the index finger of the hand gripping the finger loop, pivots the end effector; and the rotate control, which is also actuated by the same index finger, rotates the tubular barrel and attached end effector. The endoscopic surgical instrument may also be configured to include electrocautery capability, an integrated endoscope, and irrigation and aspiration capabilities is also disclosed.

54 Claims, 21 Drawing Sheets

5,827,323
Page 2

U.S. PATENT DOCUMENTS

| | | |
|---|---|---|
| 5,275,615 | 1/1994 | Rose . |
| 5,281,220 | 1/1994 | Blake, III . |
| 5,282,806 | 2/1994 | Haber et al. . |
| 5,282,807 | 2/1994 | Knoepfler . |
| 5,282,826 | 2/1994 | Quadri . |
| 5,300,081 | 4/1994 | Young et al. . |
| 5,308,358 | 5/1994 | Bond et al. . |
| 5,314,445 | 5/1994 | Heidmueller née Degwitz et al. . |
| 5,318,589 | 6/1994 | Lichtman . |
| 5,330,502 | 7/1994 | Hassler et al. . |
| 5,350,355 | 9/1994 | Sklar . |
| 5,350,391 | 9/1994 | Iacovelli . |
| 5,354,311 | 10/1994 | Kambin et al. . |
| 5,368,606 | 11/1994 | Marlow et al. . |
| 5,374,277 | 12/1994 | Hassler . |
| 5,383,888 | 1/1995 | Zvenyatsky et al. . |
| 5,403,342 | 4/1995 | Tovey et al. . |
| 5,474,571 | 12/1995 | Lang . |
| 5,536,251 | 7/1996 | Evard et al. . |

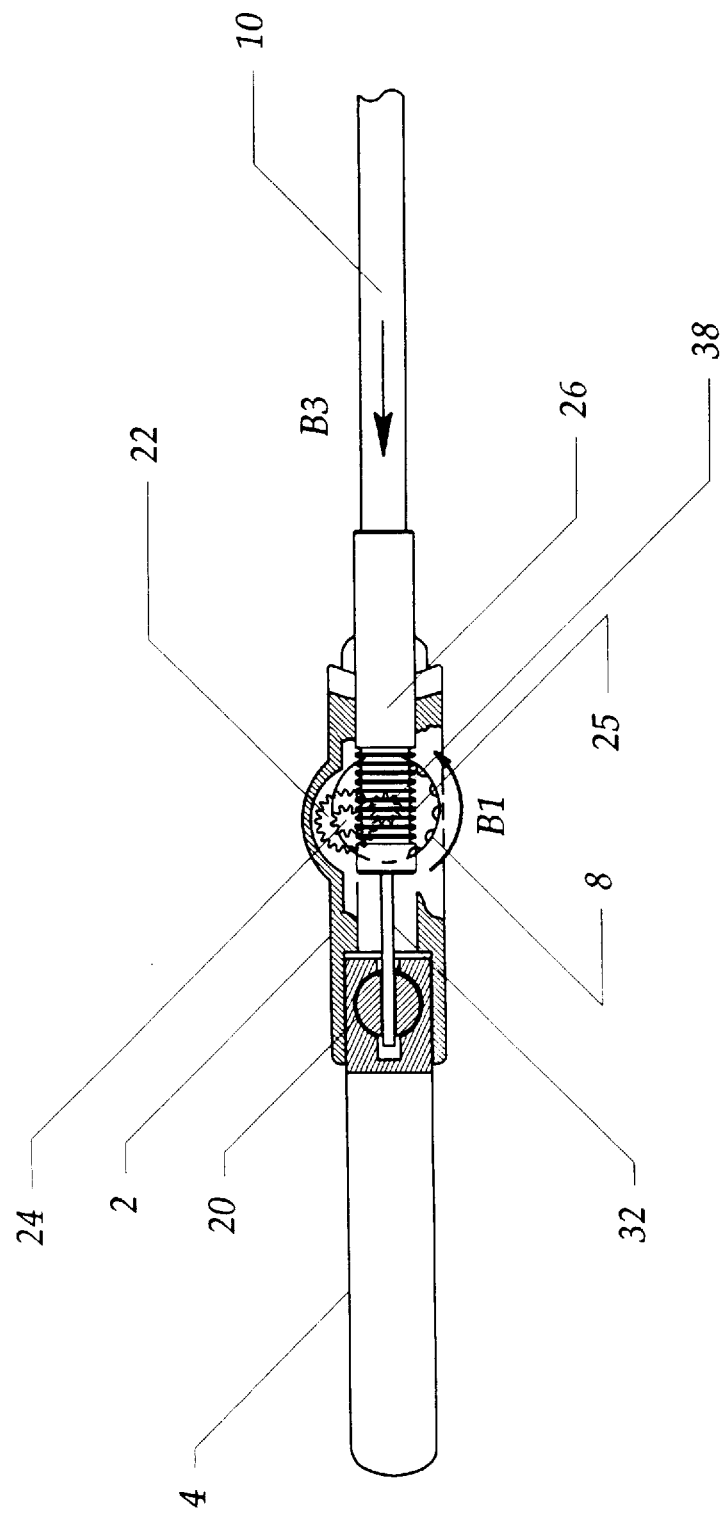

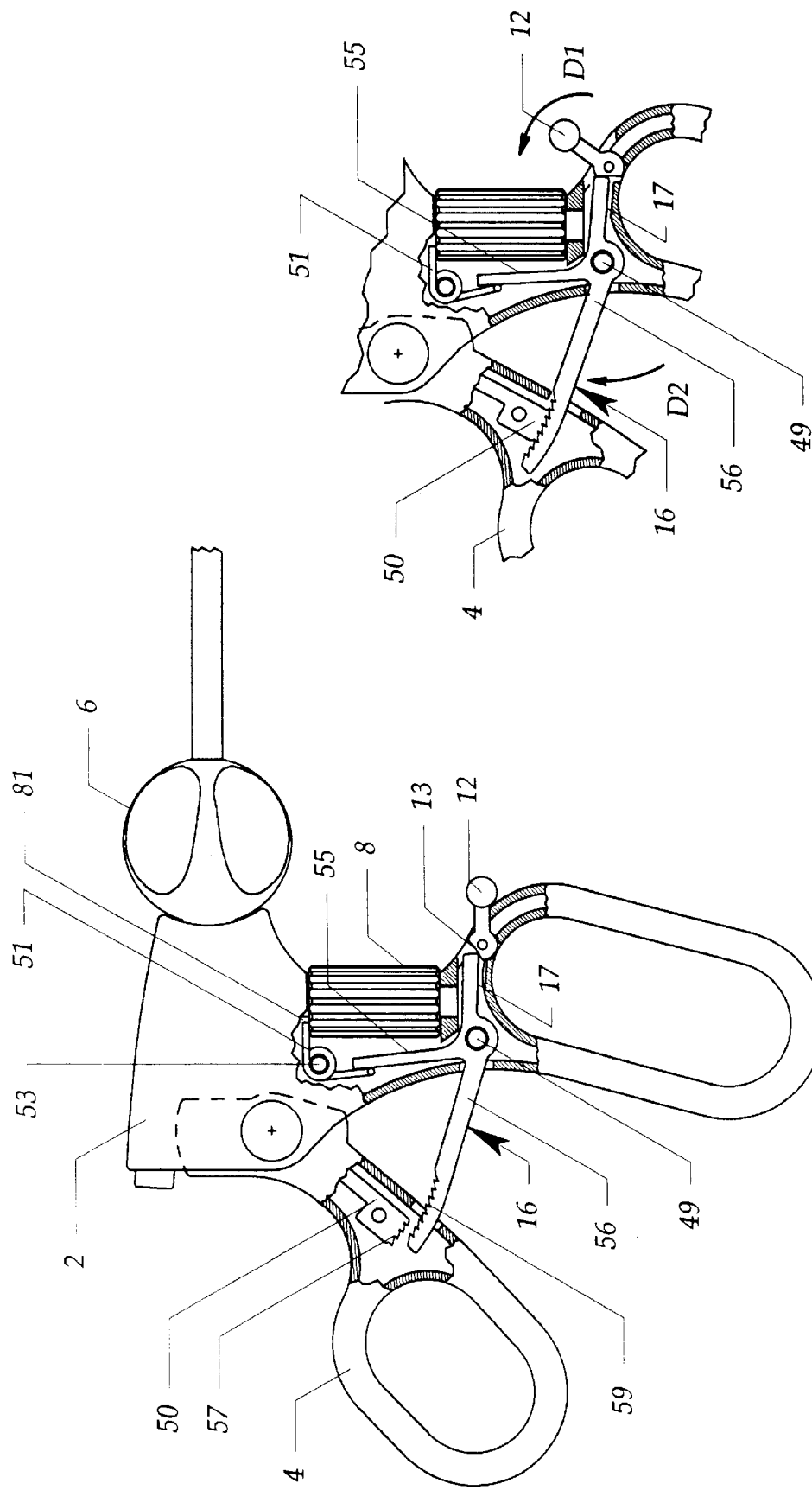

SURGICAL INSTRUMENT FOR ENDOSCOPIC AND GENERAL SURGERY

CROSS REFERENCE TO RELATED APPLICATIONS

This application is a continuation-in-part of application Ser. No. 08/471,988, filed Jun. 6, 1995; Ser. No. 08/471,988 being a continuation-in-part of application Ser. No. 08/295,352, filed Aug. 24, 1994 and previously abandoned in favor of continuation application Ser. No. 08/671,820, filed Jun. 25, 1996; Ser. No. 08/295,352 being a continuation of application Ser. No. 08/095,739, filed Jul. 21, 1993 and previously abandoned. The present application also relates to, and applicants' claim the benefit under 35 U.S.C. § 120 of the earlier filing date of, international application No. PCT/US95/13977, which was filed Oct. 11, 1995 and which designates the United States.

BACKGROUND OF THE INVENTION

The present invention relates generally to the field of endoscopic surgical instruments.

Endoscopy (e.g., laparoscopy, thoracoscopy and arthroscopy) is a form of surgery that involves visualizing the interior of the body using an illuminating optical instrument, an endoscope. The endoscope and other surgical instruments are introduced into the body through small puncture orifices.

Endoscopy, in the form of laparoscopy, traditionally has been used almost exclusively for gynecological surgery. However, physicians specializing in other fields have begun to recognize the diagnostic and operative value of endoscopy.

The advantages of endoscopic surgery include: procedures may be performed on an outpatient basis; surgeons are given the opportunity to view intra-abdominal viscera without performing a laparotomy, a large incision of the abdominal wall; small puncture ports or wounds are created rather than large incisions, lessening trauma; patient and insurer medical costs are reduced by shorter hospital stays; and postoperative patient discomfort is reduced, with a probable reduction in recovery times. Thus, there is a substantial interest in and need for providing task specific surgical instruments particularly adapted to general surgical procedures now being performed endoscopically.

Endoscopic procedures typically are commenced by using a device known as a trocar. The trocar comprises a cannula or trocar sleeve (a hollow sheath or sleeve with a central lumen) and a sharp obturator received in the cannula. The trocar is used to penetrate the abdominal wall or chest. The obturator is withdrawn from the cannula after the intra-abdominal end of the trocar is in the abdominal cavity, and the cannula remains in the abdominal wall throughout the surgical procedure, allowing the introduction of an endoscope and surgical instruments. Trocars are available in different sizes, as are cannula, to accommodate various sizes and numbers of instruments.

Surgical instruments designed specifically for endoscopic procedures have taken the form of a specialized implement (hereinafter called an end effector) attached to a distal end of a long, narrow tubular barrel. A handle attached to the opposite, proximal end of the tubular barrel usually has an associated control for operating the end effector, and may have a second control for rotating the shaft and end effector. A linkage extends through the tubular barrel and links the handle controls to the end effector.

Generally, in order to fit through the small diameter ports or incisions, an instrument is designed for a single, dedicated, specialized purpose. Ideally, a surgeon selects instruments according to his preferences and according to the procedure at hand. However, because of the costs involved with using additional instruments and the time associated with removing one and inserting another, a surgeon is inclined to make do with the instruments of initial use even though another instrument may be more suitable for the immediate task. Therefore, it is desirable that a single instrument be capable of performing a variety of tasks. It is also desirable that such a multifunctional instrument be easy to use and control, preferably with a single hand.

Thus, it is an object of the invention to provide an endoscopic surgical instrument which enhances a surgeon's capability and dexterity, yet requires a minimum number of endoscopic ports.

It is a further object of the invention to provide an improved surgical instrument with precise and intuitive one-handed controls for articulating, rotating and operating the surgical instrument end effector.

Another object of the present invention is to provide a miniature endoscopic instrument, 2 or 3 mm in diameter, designed to pass through trocar sleeves or endoscopic ports of various sizes, thereby permitting its use in minimally invasive procedures.

Still another object of the invention is to provide an instrument with extended functionally so as to be capable of performing a variety of tasks. Additional functions such as electrocautery, suction/irrigation, visualization port(s) and trigger lock allow the surgeon to work faster with fewer instruments.

SUMMARY OF THE INVENTION

In general, the invention is an endoscopic surgical instrument capable of performing a variety of surgical tasks, while offering true single-hand operation via manual controls.

The surgical instrument which incorporates the invention includes a tubular barrel with a handle at its proximal end and an end effector at its distal end. A linkage extends through the tubular barrel and connects the handle with the end effector. The end effector comprises two working pieces, each piece being pivotally attached directly to the distal end of the tubular barrel.

The handle includes a stationary portion permanently fixed in alignment with the longitudinal axis of the tubular barrel. In the preferred configuration, the instrument's handle has a grip portion which is a stationary finger loop designed to receive at least a middle finger, and perhaps also an index finger. The finger loop is attached to the stationary portion of the handle in a manner which does not allow movement of the finger loop with respect to the stationary portion or the tubular barrel.

The handle further includes a thumb loop lever attached to the stationary portion of the handle. The thumb loop lever is configured so as to be operable with the thumb of the same hand which grips the finger loop. Movement of the thumb loop lever with the thumb in a first direction increases the angle between the two working pieces of the end effector, and movement in the reverse direction decreases the angle. Thus, by reciprocal movement of the thumb loop lever, the end effector working pieces are alternately caused to move toward and away from one another in a "scissoring" action.

The handle of the instrument may also include a control for locking the thumb loop lever in a fixed position relative to the handle. Thus, the locking control prevents an increase in the angle between the end effector working pieces (for example, to keep the end effector clamped onto tissue). In preferred form, the locking control is a lock-and-release lever that may be operated by the same hand that grips the handle, and preferably by the index finger of that hand.

The handle also includes a fingerwheel roller located on the stationary portion of the handle. The fingerwheel roller is positioned on the instrument's handle in a way which allows rotation of the fingerwheel roller by the index finger of the same hand which grips the instrument through the finger loop. Rotating the fingerwheel roller with the index finger in a first direction pivots both of the end effector working pieces simultaneously away from alignment with the longitudinal axis of the tubular barrel.

Also, rotating the fingerwheel roller in the reverse direction pivots the end effector pieces simultaneously toward alignment with the longitudinal axis of the tubular barrel. Thus, the fingerwheel roller allows the surgeon to pivot the end effector pieces through an arc of up to 110° and thereby accurately position the end effector at the surgical site.

In the preferred configuration, the handle further includes a rotatable knob positioned around the proximal end of the tubular barrel. The rotatable knob is rotatable by the same index finger that operates the fingerwheel roller. The rotatable knob is affixed to the tubular barrel so, as the knob is rotated, the tubular barrel and attached end effector rotate about the longitudinal axis of the tubular barrel.

Thus, the surgical instrument which incorporates the invention described herein provides single-hand, manual control over three degrees of motion of an end effector—"scissoring", pivoting, and rotation.

The "scissoring" action of the end effector, resulting from movement of the thumb loop, and the pivoting of both pieces of the end effector, resulting from rotation of the fingerwheel roller, are accomplished by the interaction of the linkage on the end effector. That interaction will now be generally described.

The linkage of the instrument, in the preferred configuration, includes a first and a second elongated member. The first and second elongated members are connected respectively to the first and second end effector working pieces. Movement of the thumb loop lever translates the first elongated member relative to the stationary second elongated member, handle and tubular barrel. This relative movement causes the first end effector working piece to pivot with respect to the second working piece, thereby causing a change in the angle between the two working pieces of the end effector. Thus, it can be seen that reciprocating movement of the thumb loop lever results in a "scissoring" action of the two working pieces of the end effector.

In addition, rotation of the fingerwheel roller translates the tubular barrel relative to the stationary piece of the handle, while the elongated members are held stationary relative to the stationary piece. This relative movement of the tubular barrel with respect to both elongated members causes the end effector pieces to pivot simultaneously and in the same direction. Because the action of the fingerwheel roller does not cause a significant relative movement between the elongated members, the angle between the end effector pieces remains substantially constant while the end effector pieces are being pivoted. This substantially constant angle provides significant benefit to the surgeon because it allows precise and predictable positioning of the end effector during the pivoting procedure. Such precise positioning is of particular benefit, for example, when the end effector is pivoted while grasping an object or tissue.

The fingerwheel roller is coupled to the tubular barrel via a force multiplier mechanism. In the preferred embodiment, the force multiplier comprises a set of gears which interact with a rack portion on a hub which surrounds a proximal portion of the tubular barrel. Use of a force multiplier is particularly beneficial in this invention because it allows subtle and precise control over the pivot position of the end effector while only requiring relatively light finger pressure on the fingerwheel roller.

In addition to the features and functions which are summarized above, an instrument which incorporates the subject invention may also be configured to include: (i) electrocautery capability; (ii) an integrated endoscope; and (iii) irrigation and aspiration capabilities.

With respect to electrocautery capability, in the preferred embodiment, the handle has a plug for connecting the surgical instrument to a source of electrical current such as an electrosurgical generator. There is a conductive path from the plug through the linkage extending through the tubular barrel to the end effector, thereby providing electrical current to an area of interest via the end effector.

With regard to the integrated endoscope configuration, the tubular barrel may be configured so as to have a separate lumen which extends through the length of the tubular barrel. The lumen may accommodate an endoscope. For entry into the lumen there is a proximal port and for exit from the lumen there is a distal port. The distal port may be positioned just proximal of the end effector and angled so that when the endoscope protrudes from the distal port, the entire end effector is in the field of view of the endoscope.

In another aspect of the integrated endoscope configuration, the end effector may be designed to grasp and manipulate a distal end of an endoscope that is inserted into the lumen. Such an end effector may have a piece that has a loop or some other device that can be aligned with the lumen's distal port. Thus, as the endoscope is pushed through the lumen, it can be guided through the loop. Then, by manipulating the end effector with the controls on the handle, the orientation of the endoscope is altered. Therefore, the end effector may be used to position an endoscope to look around an area of interest in any direction a surgeon desires.

Finally, in regard to the irrigation/aspiration configuration of the invention, there may also be more than one lumen extending through the tubular barrel. With multiple lumens, one or more of the lumens may be adapted for providing irrigation fluid to an area of interest, and one or more other lumens provided with suction for aspirating fluid from the area of interest.

BRIEF DESCRIPTION OF THE DRAWINGS

FIG. 4 is a top view, partially in section and with parts cut away, of a portion of the embodiment of the instrument shown in FIG. 3A.

FIG. 5A is a side elevational view, partially in section, of a handle portion of the embodiment of the instrument shown in FIG. 3A, showing a lock-and-release lever 12 in a released position.

FIG. 5B is similar to that of FIG. 5A but showing the lever 12 in a locked position.

DESCRIPTION OF THE PREFERRED EMBODIMENTS

Figure 1:
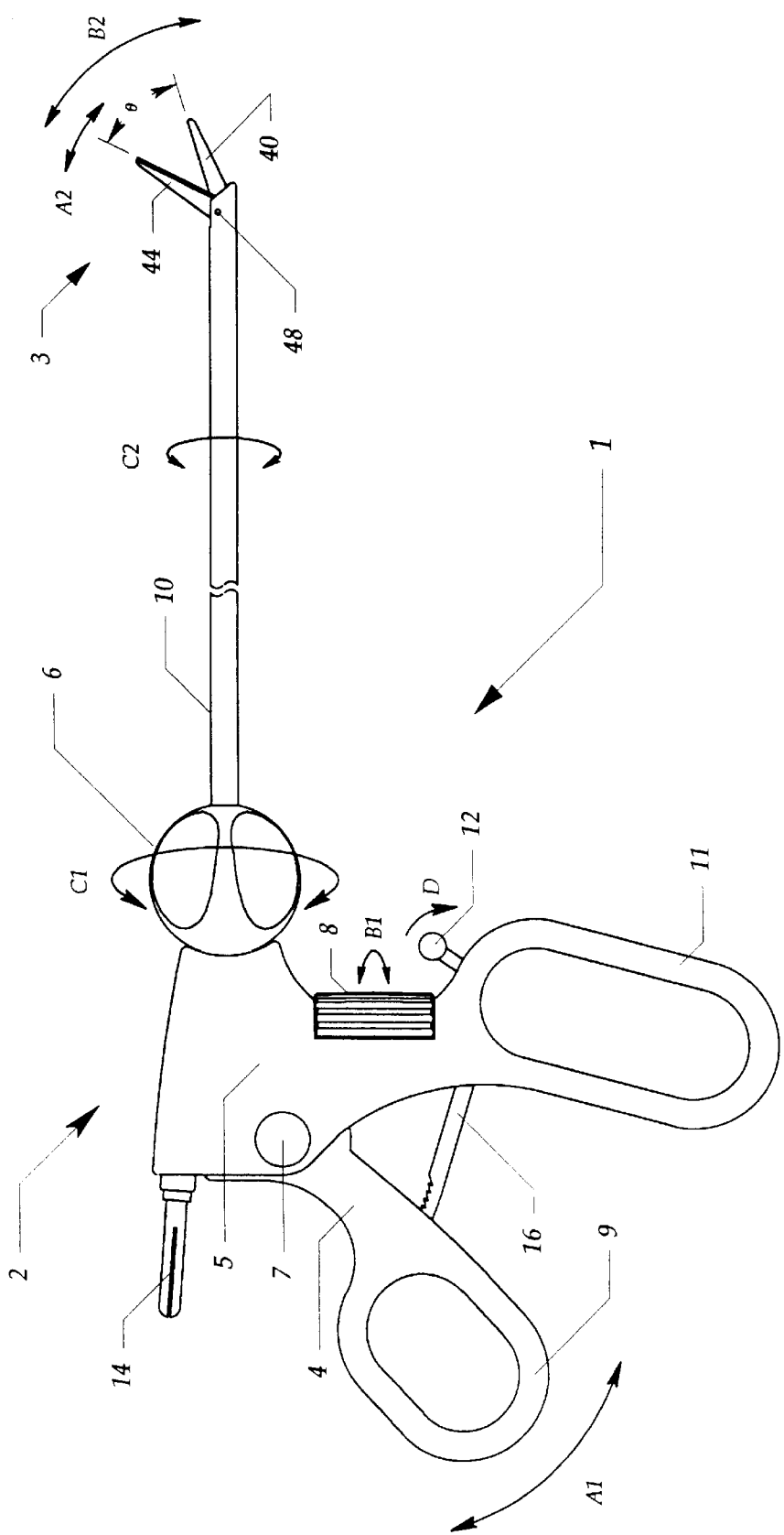
FIG. 1 is a side elevational view of a surgical instrument in accordance with the invention.

Shown in FIG. 1 is an endoscopic surgical instrument 1 which incorporates the invention described herein. The instrument 1 includes an elongated tubular barrel 10; a handle 2 attached to the proximal end of the tubular barrel 10; and an end effector 3 attached to the distal end of the tubular barrel 10. In the preferred embodiment, the handle 2 is fabricated from a molded plastic and the tubular barrel 10 is fabricated from fiber reinforced plastic. Of course, a variety of other materials may be used for the fabrication of handle 2 and tubular barrel 10.

The end effector 3, which is fabricated from stainless steel in the preferred embodiment, may be one of a variety of devices which are useful for performing a surgical task. In FIG. 1, the end effector 3 is depicted as a scissors. Other end effectors may also be used with the surgical instrument 1, for example, dissector jaws, graspers, extractors, clamps, forceps, retractors, a biopsy tool, and any other similar device which would be of assistance during surgery.

The end effector 3 in FIG. 1 is made up of two separate, blade-like end effector pieces 40 and 44. The end effector pieces 40, 44 are attached to the distal end of the tubular barrel 10 by a pin 48 that extends through the tubular barrel 10 perpendicular to its longitudinal axis. The pin 48 extends through a hole (not shown in FIG. 1) cut through the proximal end of each end effector piece 40, 44. The end effector pieces 40 and 44 are thus independently pivotable about pin 48. The pivotable movement is toward and away from the longitudinal axis of the tubular barrel 10, as indicated by arrow B2.

Associated with the handle 2 are controls for manipulating the end effector 3 to accomplish a variety of surgical tasks. First, for accomplishing "scissoring" action of the end effector 3, the handle 2 has a trigger lever 4. The trigger lever 4 is pivotally attached by pin 7 to a stationary piece 5 of the handle 2. Pivotal movement of the trigger lever 4 in either direction, as indicated by arrow A1, effects pivotal movement of the end effector piece 44, as indicated by arrow A2. On the other hand, pivotal movement of the trigger lever 4 does not result in movement of end effector piece 40. Therefore, actuating the trigger lever 4 alters the operating angle $\theta$ between the two end effector pieces 40 and 44 by moving end effector piece 44 toward or away from stationary end effector piece 40.

Fingerwheel roller 8 is provided on handle 2 for pivoting both end effector pieces 40 and 44 simultaneously and in the same direction, as indicated by arrow B2. The fingerwheel roller 8 is attached to the stationary piece 5 of the handle 2 so that the roller 8 can be rotated in either direction, as indicated by arrow B1, about a longitudinal axis of the fingerwheel roller 8. When viewed from the top of instrument 1, rotation of the fingerwheel roller 8 in a clockwise direction effects simultaneous movement of both end effector pieces 40 and 44 toward an alignment with the longitudinal axis of the tubular barrel 10 (the "longitudinally extended position"), as indicated by the clockwise portion of arrow B2. Similarly, counterclockwise rotation of the fingerwheel roller 8 results in pivoting both end effector pieces 40, 44 away from the longitudinally extended position. Assuming the trigger lever 4 is not actuated while the fingerwheel roller 8 is being rotated, rotation of the fingerwheel roller 8 will cause the end effector pieces 40 and 44 to pivot simultaneously in the same direction while maintaining a substantially constant operating angle $\theta$ between the two end effector pieces 40 and 44.

To lock an operating angle $\theta$ constant between the end effector pieces 40 and 44, the handle 2 has a lock-and-release lever 12. The lever 12 is pivotably movable with respect to the stationary piece 5 of the handle 2. The lever 12 is shown in FIG. 1 in a locked position, and can be pivoted, as indicated by arrow D, into a released position (not shown). In the locked position, a ratchet bar 16 prevents the trigger lever 4 from opening further, and thus prevents the opening of the end effector pieces 40 and 44. Pivoting the lock-and-release lever 12 in the direction indicated by arrow D into the released position (not shown), causes the ratchet bar 16 to release the trigger lever 4 so that it can be opened freely, as will be discussed in more detail below. The lock-and-release lever 12 remains in the released position until the surgeon moves it into the locked position.

The handle 2 includes a rotation knob 6 for rotating the entire tubular barrel 10, as indicated by arrow C2, and consequently for rotating the attached end effector 3. The knob 6 is rotatable with respect to the stationary piece 5 of the handle 2, in a manner indicated by arrow C1. The tubular barrel 10 is rotatably secured to the knob 6 so that the knob 6 and barrel 10 rotate as one.

The design of the handle 2 enables a surgeon to grasp the surgical instrument in either hand. A thumb loop 9 on the trigger lever 4 is designed to receive the surgeon's thumb, and a finger loop 11 on the stationary piece 5 is designed to receive the surgeon's middle and ring fingers. This leaves the surgeon's index finger free to operate the rotation knob 6, the fingerwheel roller 8, and the lock-and-release lever 12. The design of the surgical instrument 1, and in particular its handle 2 design, therefore offers true single-handed operation. In addition, because the stationary piece 5 of the handle 2 remains in a fixed spatial relationship with the distal end of the tubular barrel 10, the surgical instrument 1 offers the surgeon a high degree of precision in positioning and moving the end effector 3.

FIGS. 2A–D show the distal portion of actuating mechanism of the end effector 3. The end effector pieces 40 and 44 are pivotally attached to the distal end of tubular barrel 10. When the end effector pieces 40 and 44 are not pivoted (i.e., the pieces 40 and 44 are in the longitudinally extended position), the end effector pieces 40 and 44 do not protrude outside of a defined diameter of the tubular barrel 10. In a preferred embodiment, the defined diameter is approximately 5 mm, which is small enough to allow the instrument 1 to readily pass through either a trocar sleeve (not shown) as small as 5 mm or a laparoscopic port of similar dimension (not shown). However, in alternate embodiments, the defined diameter of the tubular barrel 10 may be 2 or 3 mm.

Figure 2A:
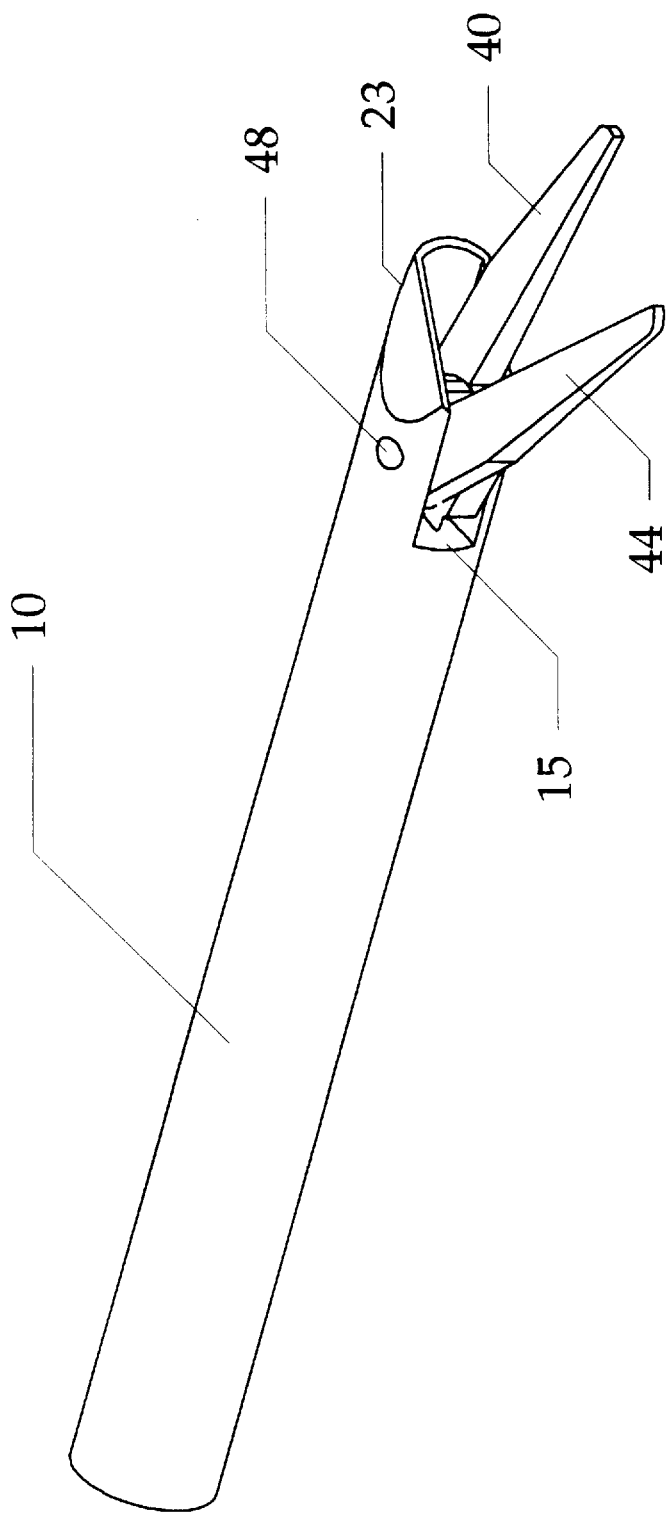
FIG. 2A is an isometric view of a portion of the instrument of FIG. 1, showing an end effector.
Figure 2B:
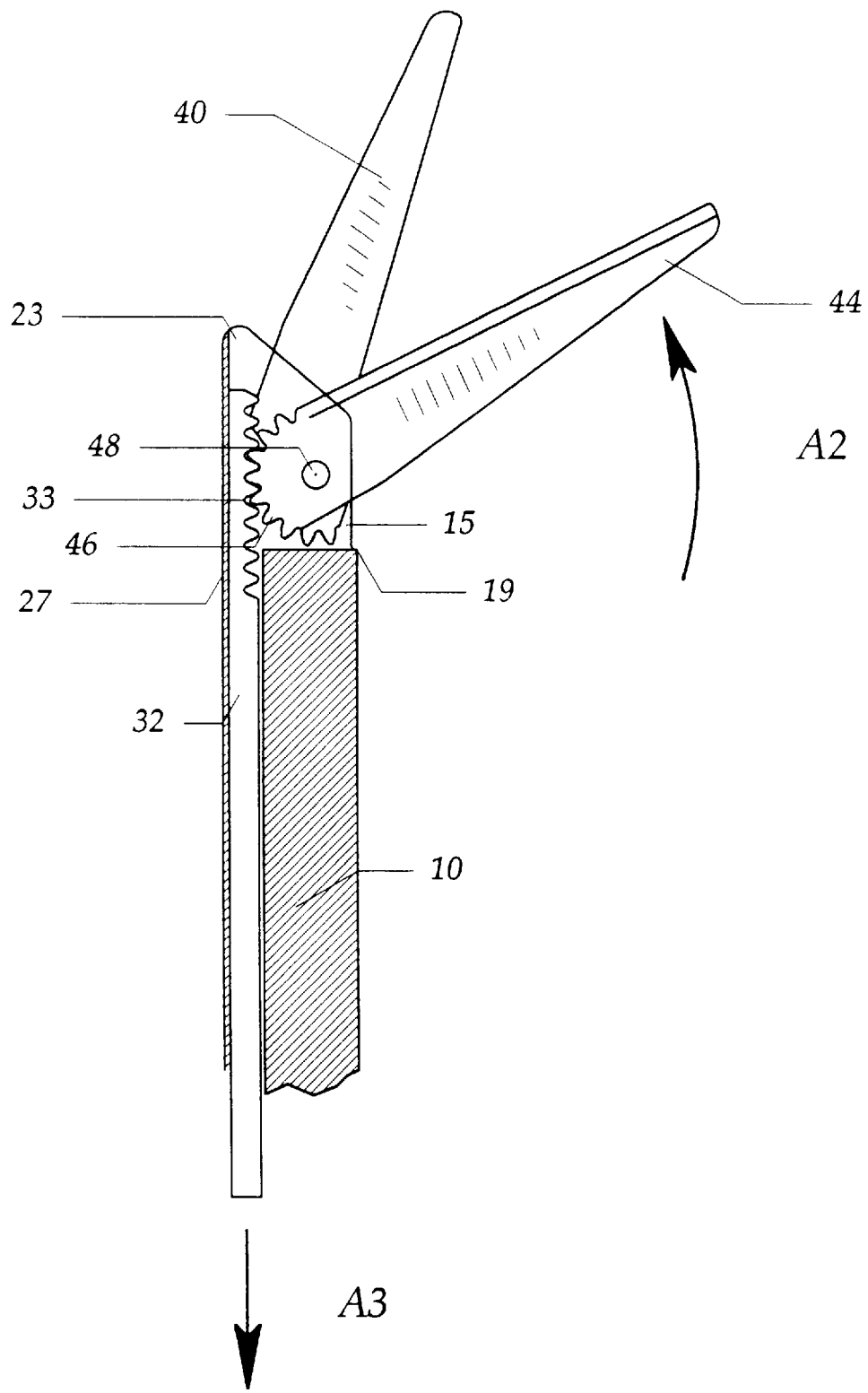
FIG. 2B is a side elevational view, with parts shown transparently to show internal parts, of a portion of the instrument of FIG. 1, including a pivoting mechanism for the end effector.
Figure 2C:
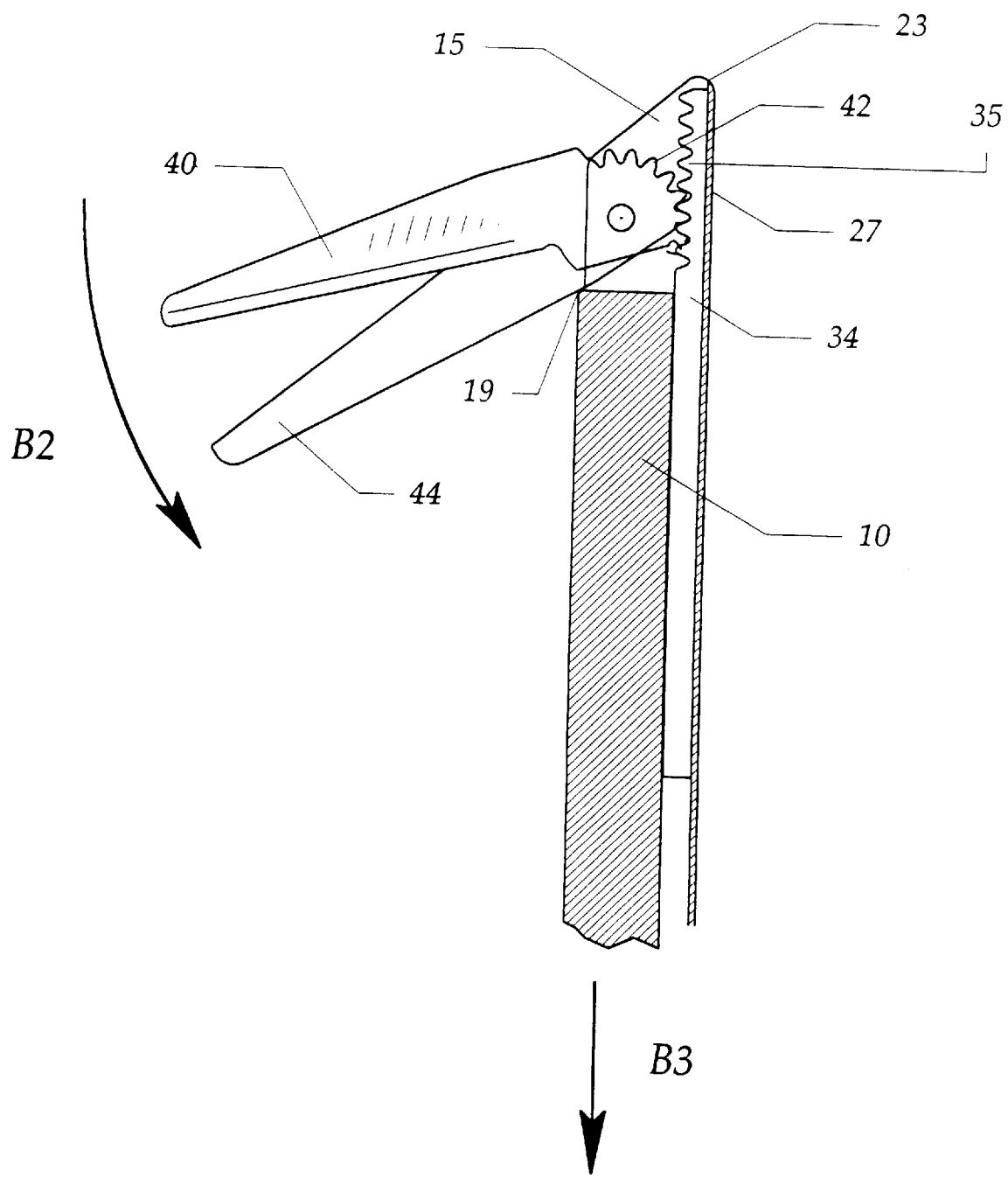
FIG. 2C is a side elevational view similar to that of FIG. 2B, but from an opposite side.

A notch 15, shown in FIG. 2A, in one side of the tubular barrel 10 allows the end effector pieces 40 and 44 to be pivoted away from the longitudinally extended position. The end effector pieces 40 and 44, in the embodiment shown, can be pivoted about 110° from the longitudinally extended position. FIG. 2C shows end effector piece 44 pivoted 110° from the fully extended position. When pivoted 110°, end effector piece 44 abuts a proximal edge 19 of the notch 15, and hence cannot be further pivoted.

Figure 2D:
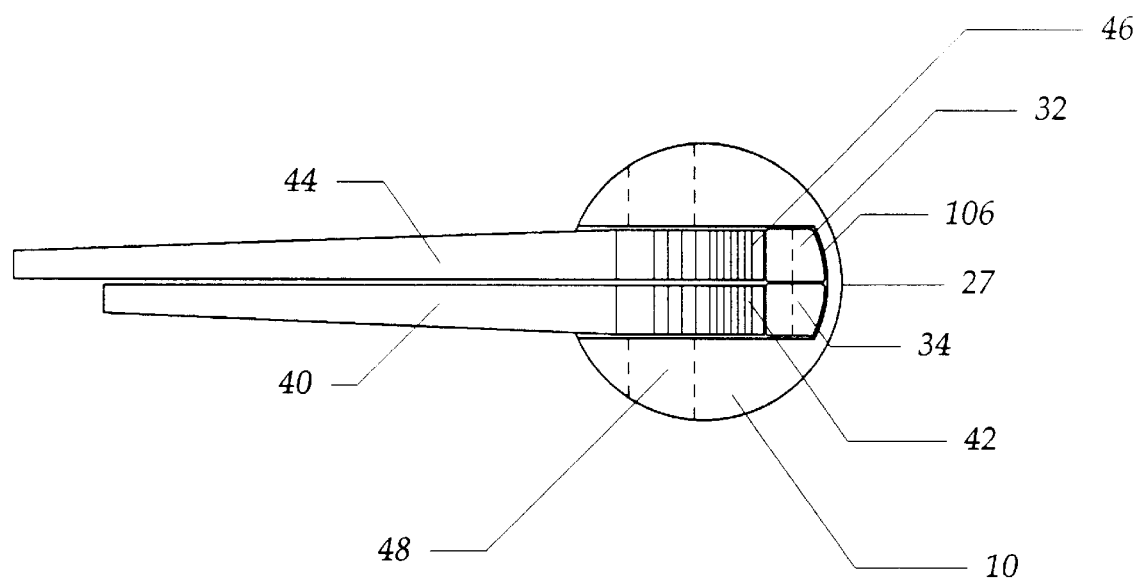
FIG. 2D is an end view of the instrument of FIG. 1, from the end effector end of the instrument.

Each end effector piece 40 and 44 has on the periphery of its proximal end a set of gear teeth 42 and 46. Gear teeth 42 for piece 40 are shown in FIGS. 2C and 2D, and gear teeth 46 for piece 44 are shown in FIGS. 2B and 2D. Slidably disposed within the tubular barrel 10 is a first elongated member 32 (FIGS. 2B and 2D) and a second elongated member 34 (FIGS. 2C and 2D). Elongated members 32 and 34, in the preferred embodiment, are fabricated from a high strength stainless alloy wire and are constrained inside channel 106 (FIG. 2D). The dimensions of channel 106 are selected to be large enough to cause minimal friction on elongated members 32 and 34, but small enough to prevent lateral buckling of elongated members 32 and 34. Like the end effector pieces 40 and 44, the elongated members 32 and 34 are separate and independent of one another, as can be seen in FIG. 2D.

Now referring to FIGS. 2B and 2C, each elongated member 32 and 34 has at its distal end a rack 33 and 35. Rack 33 for member 32 is shown in FIG. 2B, and rack 35 for member 34 is shown in FIG. 2C. The racks 33 and 35 of elongated members 32 and 34 are prevented from engaging tissue during a surgical procedure by an angular protrusion 23 in the distal end of the tubular barrel 10. Rack 33 of elongated member 32 mates with gear teeth 46 of end effector piece 44 (FIG. 2B), and rack 35 of elongated member 34 mates with gear teeth 42 of end effector piece 40 (FIG. 2C). The elongated members 32 and 34, and particularly their racks 33 and 35, are held in engagement with the gear teeth 42 and 46 of the end effector pieces 40 and 44 by a back portion 27 of the tubular barrel 10 (i.e., an interior surface of channel 106), upon which the elongated members 32 and 34 bear.

Relative movement between elongated member 32 or elongated member 34 and the tubular barrel 10 effects pivoting of the respectively mated end effector piece 40 or 44. Referring to FIG. 2B, "scissoring" is effected when elongated member 32 is translated within the tubular barrel 10. This translation causes the mated end effector piece 44 to pivot. For example, when the elongated member 32 is translated proximally, as indicated by arrow A3 in FIG. 2B, end effector piece 44 pivots toward the longitudinally extended position, as indicated by arrow A2. The reverse occurs when the elongated member 32 is translated distally. As will be seen later, a surgeon causes the elongated member 32 to be translated by actuating the trigger lever 4 (FIG. 1).

As shown in FIG. 2C, for simultaneous pivoting of both end effector pieces 40 and 44 in the same direction, the tubular barrel 10 is translated with respect to elongated members 32 and 34. In other words, the tubular barrel 10 is pulled toward, and pushed away from, the handle 2 (not shown in FIG. 2C) while the elongated members 32 and 34 are held stationary with respect to the handle 2. Translating the tubular barrel 10 proximally, as indicated by arrow B3, causes both end effector pieces 40 and 44 to pivot as indicated by arrow B2. The reverse occurs when the tubular barrel 10 is translated distally. As will be seen below, a surgeon causes the tubular barrel 10 to be translated and hence both end effector pieces 40 and 44 to be pivoted simultaneously, by actuating the fingerwheel roller 8 (FIG. 1).

Figure 3A:
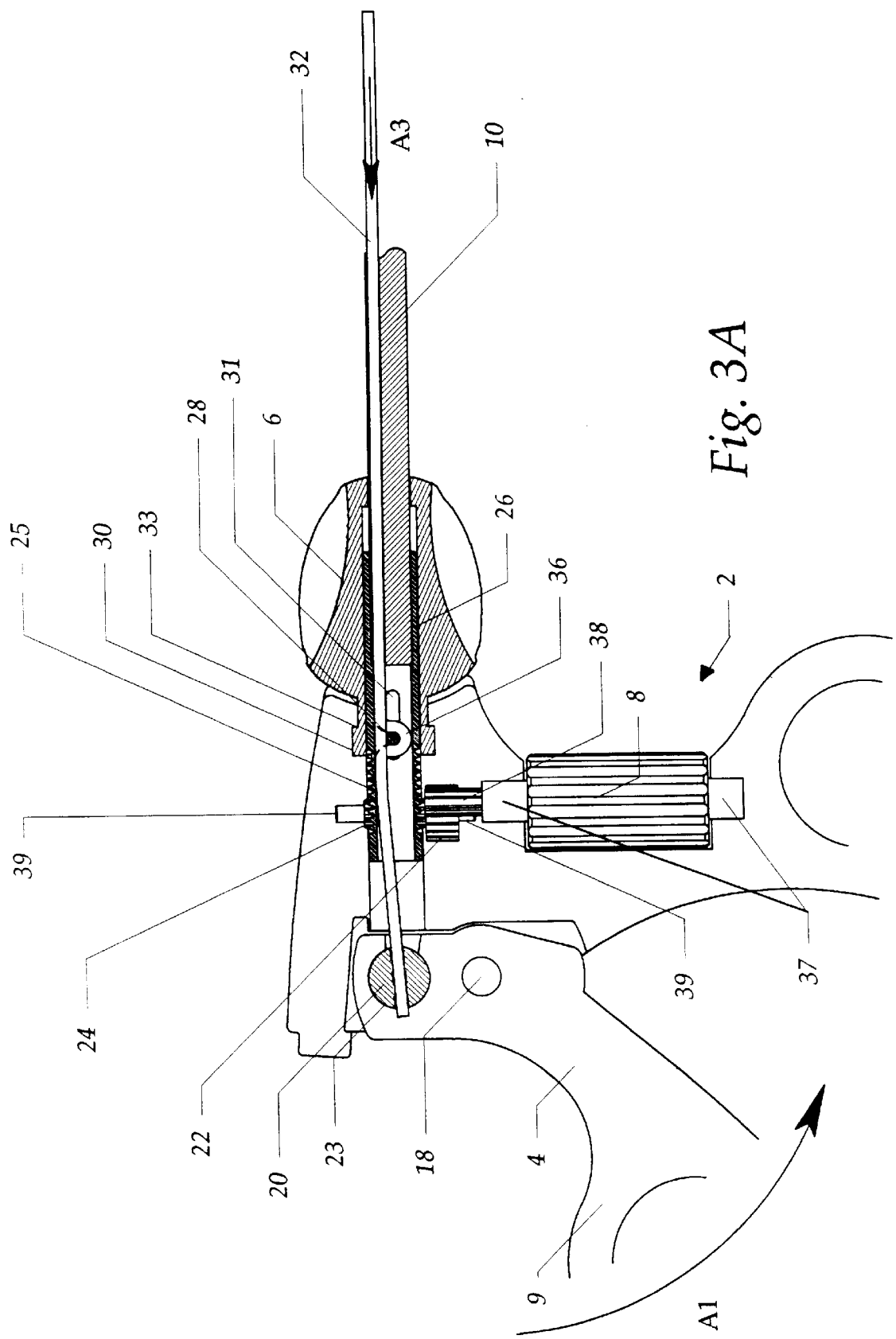
FIG. 3A is an elevational view, partially in section, of an embodiment of a portion of the instrument of FIG. 1.
Figure 3B:
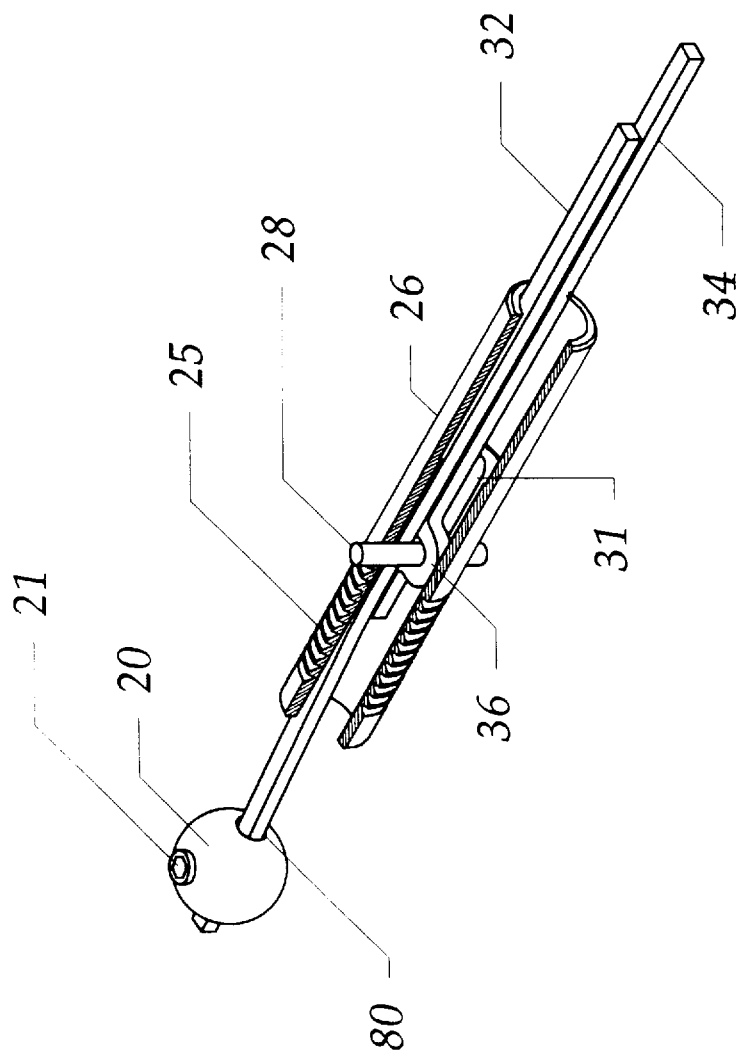
FIG. 3B is a perspective view of internal components in the portion of the instrument shown in FIG. 3A.

FIGS. 3A and 3B show how the trigger lever 4 causes the elongated member 32 to be translated within the tubular barrel 10 to cause the "scissoring" of the end effector pieces 40 and 44. As seen in FIG. 3A, the proximal end of elongated member 32 is secured to the trigger lever 4 with a ball 20 and socket 23 arrangement. As seen in FIG. 3B, the elongated member 32 extends through a bore 80 in the ball 20 and is secured to the ball 20 by a setscrew 21. Returning to FIG. 3A, it can be seen that when a surgeon squeezes the handle 2 so that the trigger lever 4 pivots about pivot point 18, as indicated by arrow A1, the elongated member 32 is pulled in the proximal direction. The ball 20 and socket 23 arrangement allows elongated member 32 to rotate within the tubular barrel 10 (which will be explained more fully below) and relieves stress on the elongated member 32 near the point where the elongated member 32 is secured to the trigger lever 4.

Now referring to FIGS. 3A–B and 4, the way in which fingerwheel roller 8 causes simultaneous pivoting of both end effector pieces 40 and 44 will be explained. (In FIG. 3B, the tubular barrel 10, trigger level 4 and stationary piece 5 have been removed for clarity). A hub 26 is secured to the outside of the tubular barrel 10, by an adhesive or mechanical crimp, so that the hub 26 and barrel 10 translate as one piece. The fingerwheel roller 8 is mounted on an axle 37, as shown in FIG. 3A. A first pinion 38 is also mounted on the axle 37 and rotates as the fingerwheel roller 8 is rotated. The first pinion 38 mates with a gear 22 (see FIG. 4), so that the first pinion 38 and the gear 22 rotate in opposite directions. The gear 22 is on a second axle 39 (see FIG. 3A) having a second pinion 24 (see FIG. 4) such that rotation of gear 22 causes rotation of second pinion 24. The second pinion 24 mates with a cylindrical rack 25 machined into the barrel hub 26 at its proximal end. Rotation of the second pinion 24 thus causes the barrel hub 26 and tubular barrel 10 to be translated axially.

Referring to the top view of FIG. 4, when the fingerwheel roller 8 and hence pinion 38 is rotated counterclockwise as indicated by arrow B1, gear 22 and second pinion 24 are rotated clockwise. Clockwise rotation of second pinion 24 pulls barrel hub 26, and hence tubular barrel 10, proximally, as indicated by arrow B3. As described above, proximal movement of the tubular barrel 10, while elongated members 32 and 34 remain stationary with respect to the handle 2 and each other, causes both end effector pieces 40 and 44 to pivot simultaneously from the longitudinally extended position.

The pinions 38, 24 and gear 22 function as a force multiplier, allowing the tubular barrel 10 to be translated with relatively light finger pressure on the fingerwheel roller 8. Alternative force multiplier mechanisms could be used. For example, a set of levers and linkages could be used, as could eccentric cams or crankshafts.

During pivoting of both end effector pieces 40 and 44, tactile feedback is provided to the surgeon by a series of detents 81 (i.e., cylindrical grooves, which are not shown in FIG. 3A) on the top of fingerwheel roller 8. A spring 51, shown in FIG. 5A, presses into detents 81. In addition to providing the surgeon with a tactile sense of how far he has pivoted the end effector pieces 40 and 44, the detents 81 also stabilize the end effector pieces 40 and 44. That is, detents 81 resist any tendency of pressure on the end effector pieces 40 and 44 to "back drive" (i.e., rotate in a direction opposite the intended direction) the fingerwheel 8 when an external force is applied to the end effector pieces 40, 44. This is particularly useful when the blades are pivoted over a full 110° and used as a small retractor.

Now referring to FIG's 3A and 3B, the way in which rotation knob 6 causes rotation of the end effector around the longitudinal axis of tubular barrel 10 will be explained. As shown in FIG. 3A, the handle 2 has a cavity 33 into which a collar 30 of the rotation knob 6 is rotatably secured. Inside the collar 30 a pin 28 extends through a longitudinal slot 31 in the barrel hub 26 and the tubular barrel 10. When the rotation knob 6 is rotated, the pin 28 causes the tubular barrel 10 and hence the end effector 3 to be rotated as indicated by arrow C2 of FIG. 1. Because the pin 28 is free to slide through longitudinal slot 31, the barrel hub 26 and tubular barrel 10 can be translated without being hindered by the pin 28. Also, because the cylindrical rack 25 on the barrel hub 26 is cut into the barrel hub 26 so as to be circular and symmetric about the axis of hub 26 (as opposed to screw-threaded), rotation of the tubular barrel 10 does not cause the barrel 10 to be translated. Thus, rotation of the tubular barrel 10 results in rotation of end effector 3, but does not cause end effector 3 to pivot.

Now referring to FIG. 3B, it can be seen that rotation of pin 28 (as a result of rotating knob 6—see FIG. 3A) causes the elongated members 32 and 34 to be rotated along with the tubular barrel 10. Elongated member 32 is disposed on one side of the pin 28 and connected to ball 20. Because ball 20 is free to rotate within its socket 23 in the trigger lever 4, when pin 28 rotates, the elongated member 32 is caused to rotate within the tubular barrel 10 (FIG. 3A).

The "U"-shaped bend 36 of elongated member 34 serves to secure the elongated member 34 so that it is not translated proximally or distally with respect to the collar 30 of the rotation knob 6 and hence with respect to the handle 2. Thus it can be seen that the elongated member 34 is held stationary when either the elongated member 32 is translated by the trigger lever 4 or the tubular barrel 10 is translated by the fingerwheel roller 8.

As shown above, "scissoring", pivoting and rotating the end effector 3 are each actuated by an independent handle control. The independence of the three functions offers the surgeon increased control. Further, it will be appreciated that more than one function may also be actuated at the same time, thus offering more flexibility to the surgeon.

FIGS. 5A–B show detail of the locking mechanism that allows the end effector pieces 40 and 44 to be "clamped" on tissue or closed during a surgical procedure and kept locked in that closed position. The locking mechanism, which is primarily positioned inside the handle 2 and trigger lever 4, includes a three-armed ratchet bar 16 that pivots about a pin 49. The spring 51, which pivots about pin 53, biases a first arm 55 so that a second arm 56 of the ratchet bar 16 is biased toward a mating catch 50. A flat cam 13, on the lock-and-release lever 12, lifts a third arm 17 of ratchet bar 16, as shown in FIG. 5A, to hold arm 56 away from mating catch 50. FIG. 5A thus shows lock-and-release lever 12 and the locking mechanism in the released position.

When the lock-and-release lever 12 is pivoted in the counterclockwise direction (illustrated by arrow D1) as shown in FIG. 5B, ratchet bar 16 is caused to rotate slightly in the clockwise direction (shown by arrow D2) by the interaction of flat cam 13 and third arm 17. Then, teeth 59 of ratchet bar 16 engage the teeth 57 of catch 50, thereby preventing the trigger lever 4 from opening further. The tooth profile 57, 59 on both the ratchet bar 16 and catch 50 is designed to keep the trigger lever 4 locked with respect to handle 2 until the trigger lever 4 is pulled again.

Figure 6:
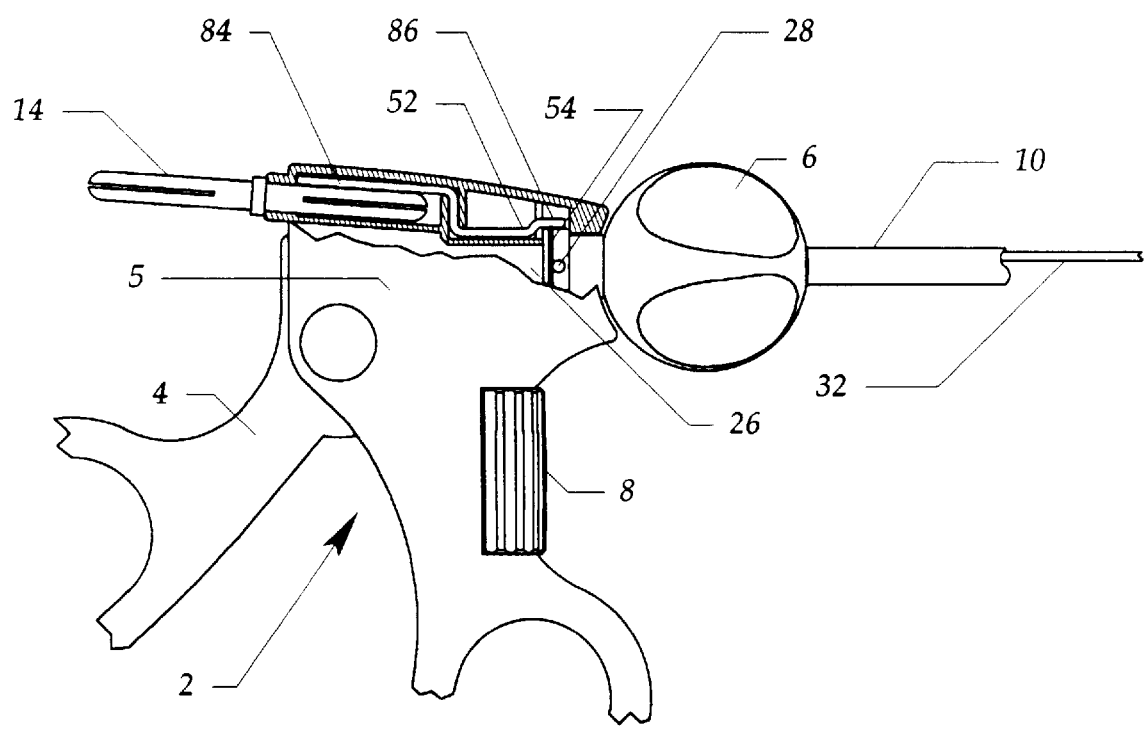
FIG. 6 is an elevational view of a portion of the instrument of FIG. 1.

The surgical instrument 1 shown in FIG. 1 is also configured to perform monopolar electrocautery. (Electrocautery is frequently required for hemostasis of bleeding during surgery.) The instrument has a plug 14, shown in FIGS. 1 and 6, on the back of the handle 2. The plug is for receiving an electrocautery cord (not shown) from an electrosurgical generator (also not shown). Shown in FIG. 6 is the conductive path from the electrocautery plug 14 to the elongated member 32, which, in turn, is electrically connected to the end effector 3. (As described above, the handle 2 is fabricated from a molded plastic and the tubular barrel 10 is fabricated from fiber reinforced plastic. Thus, neither the handle 2 nor the barrel 10 are electrically conductive.)

More specifically, the plug 14 makes electrical contact with the proximal end 84 of a cautery wire 52 disposed within the stationary piece 5 of the handle 2. A distal end 86 of the cautery wire 52 is connected to a conductive ring 54 formed around the barrel hub 26. The conductive ring 54 is electrically connected to the pin 28 which, in turn, is connected to the elongated members 32 and 34 (see FIG. 3B).

The cautery wire 52 and conductive ring 54 serve an additional purpose of providing tactile feedback to the surgeon when he is turning the rotation knob 6 and hence rotating the tubular barrel 10 and end effector 3. The cautery wire 52 is formed so that it acts as a cantilever spring, the distal end 86 of the wire 52 bearing on semi-circular detents disposed around the periphery of the conductive ring 54. The distal end 86 of the cautery wire 52 can be moved vertically. However, lateral movement of the cautery wire 52 is constrained by ribs (not shown) disposed on both sides of the wire 52.

Now turning to FIGS. 7A–7E, it can be seen that the surgical instrument 1 may also include one or more channels (that is, lumens) extending through the tubular barrel 10. Shown in FIGS. 7A–E is a surgical instrument 1 having a lumen 90 specially designed to receive a miniature flexible fiber-optic scope 62. The lumen 90 extends through nearly the entire length of the tubular barrel 10. In the preferred embodiment, the diameter of tubular barrel 10 is 5 mm. In other similarly configured embodiments, the diameter of tubular barrel 10 may be 2 or 3 mm.

Figure 7A:
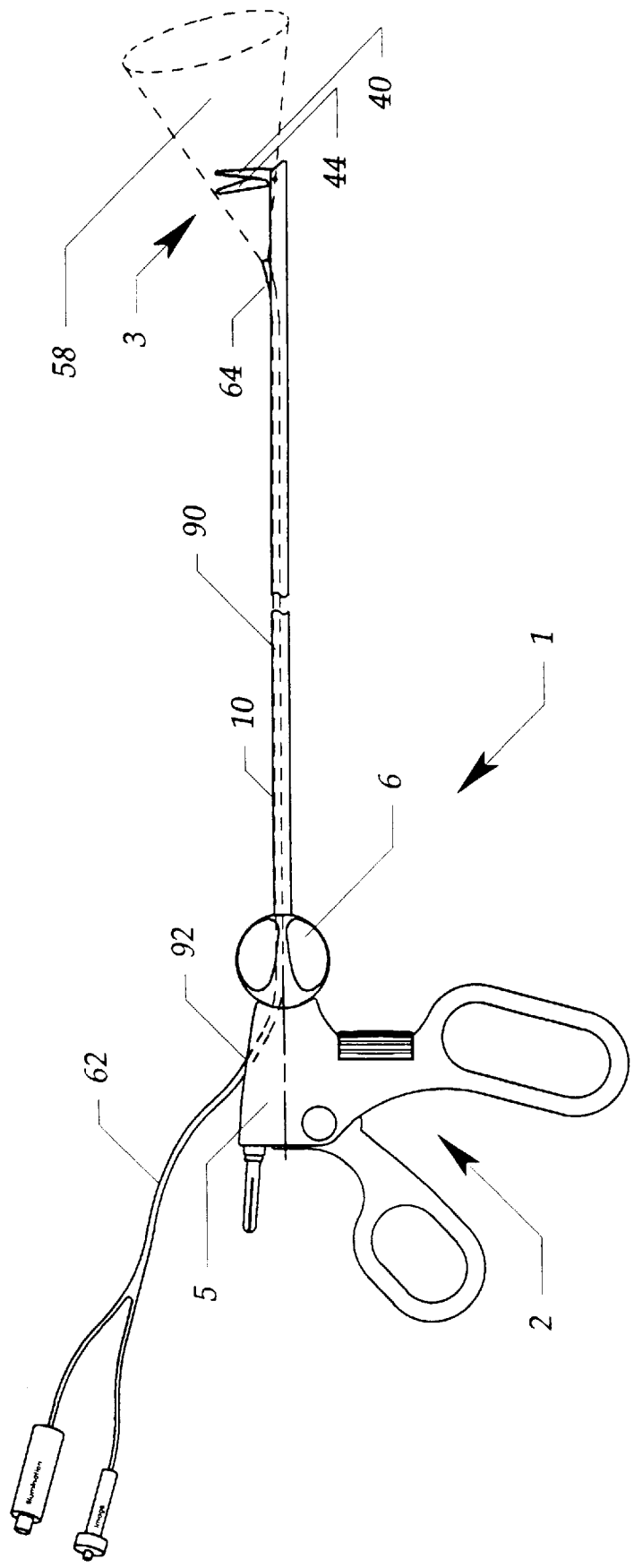
FIG. 7A is a side elevational view of an instrument in accordance with the invention having a flexible endoscope scope inserted through a lumen of the instrument.

There are three possible entry ports into the lumen 90. A first entry port 92, shown in FIG. 7A, is on the top of the stationary piece 5 of the handle 2. From entry port 92 the lumen 90 extends through the stationary piece 5 and into the tubular barrel 10.

Figure 7B:
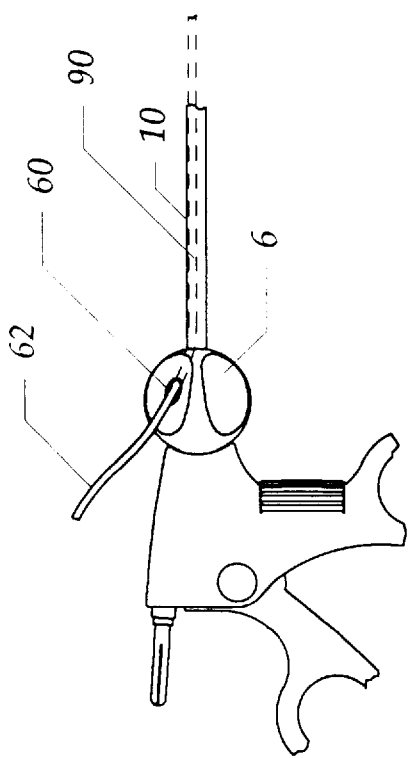
FIG. 7B is a side elevational view of a portion of the instrument of FIG. 7A with an alternative port location.

A second possible entry port 60, shown in FIG. 7B, is on the rotation knob 6. From entry port 60 the lumen 90 extends into the tubular barrel 10.

Figure 7C:
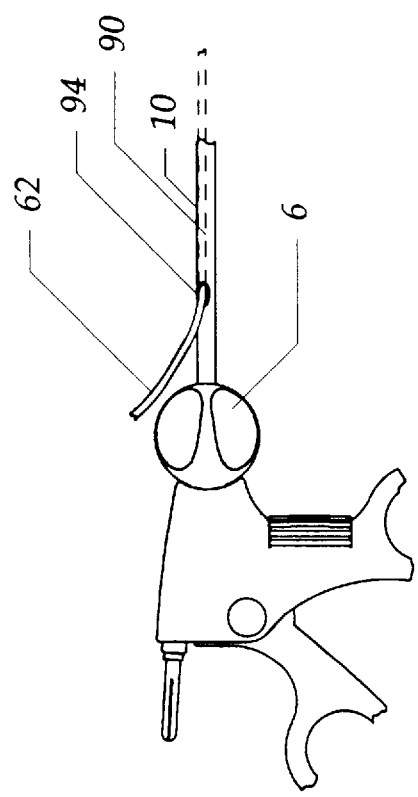
FIG. 7C is a side elevational view of a portion of the instrument of FIG. 7A with a second alternative port location.

A third possible entry port, shown in FIG. 7C, is on the tubular barrel 10 near its proximal end. When not in use, the entry ports 92, 60 and 94 may be plugged with a small stopper or sliding sleeve (neither is shown) to avoid air leaking through the instrument 1.

Figure 7D:
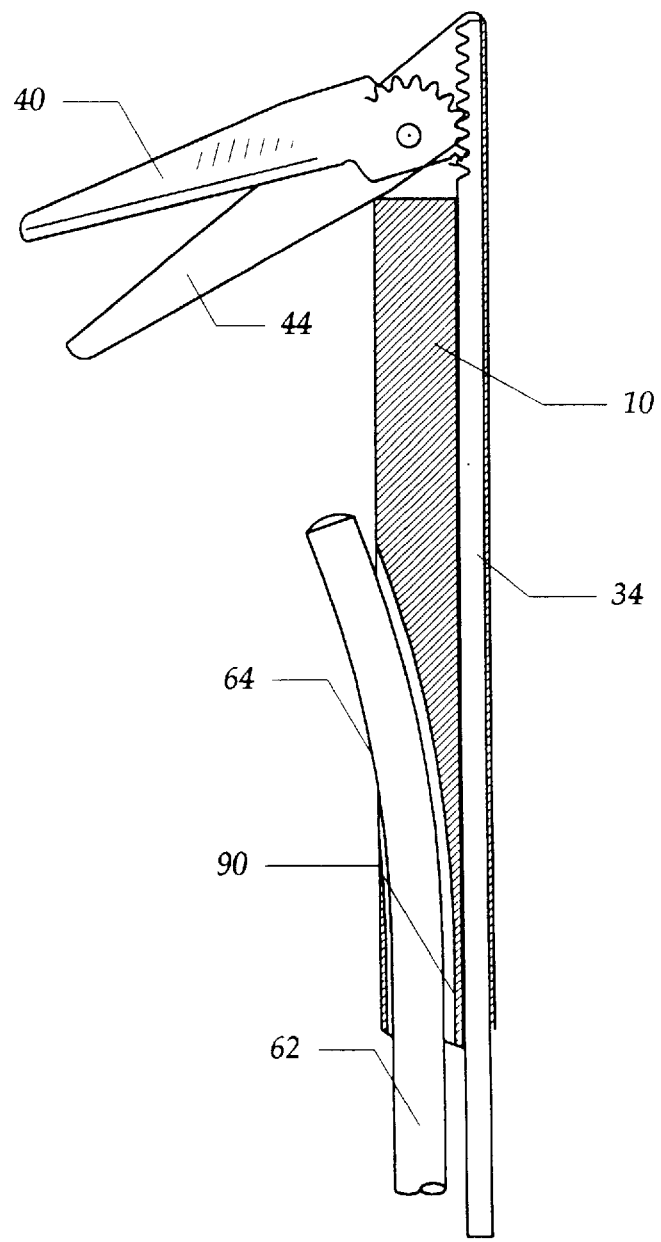
FIG. 7D is a side elevational view, partially in section, of a portion of the instrument shown in FIG. 7A.

The lumen 90 ends at an exit port 64, shown in FIG. 7A and in further detail in FIG. 7D. The exit port 64 is on the tubular barrel 10, just proximal of the end effector 3. The exit port 64 is on the side of the tubular barrel 10 toward which the end effector pieces 40 and 44 pivot. With the fiber-optic scope 62 exiting the tubular barrel 10 at exit port 64, the surgeon's field of view 58 (the periphery of which is shown in FIG. 7A in dashed lines) includes both end effector pieces 40 and 44 at any angle of pivot, as well as any anatomy of interest.

Figure 7E:
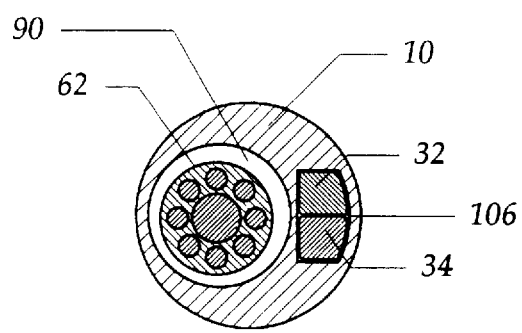
FIG. 7E is a cross-sectional view of the tubular barrel of the instrument shown in FIG. 7A.

FIG. 7E is a cross-section of the tubular barrel 10 showing the lumen 90 with the fiber-optic scope 62 inside the lumen 90. Of course, lumen 90 can accommodate other catheter devices such as a camera, and laser fiber.

Figure 8:
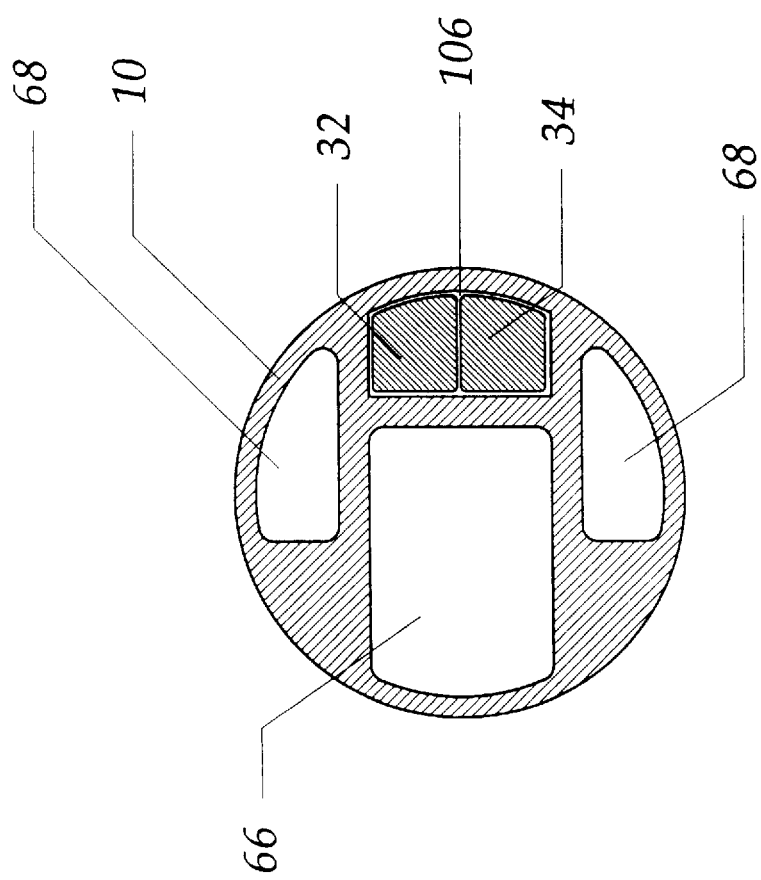
FIG. 8 is a cross-sectional view of the tubular barrel of the instrument shown in FIG. 7A, with an alternative lumen configuration than that shown in FIG. 7E.

FIG. 8 illustrates another alternative embodiment of the surgical instrument 1—in this embodiment there are multiple lumens. A cross-section of the tubular barrel 10, depicted in FIG. 8, shows a larger central lumen 66, two smaller side lumens 68 and channel 106. In the preferred embodiment, the diameter of tubular barrel 10 is 5 mm; however, other multi-lumen embodiments may be configured within a tubular barrel 10 having a diameter of 2 or 3 mm. The multiple lumens may be used in a variety of applications. In a first application, which will be described immediately below, the multiple lumens, in combination with the end effector, allow for multiple positionings of a fiber-optic catheter. In a second application, which will be described after the fiber-optic catheter positioning application, the multiple lumens provide for suction and irrigation.

Figure 9:
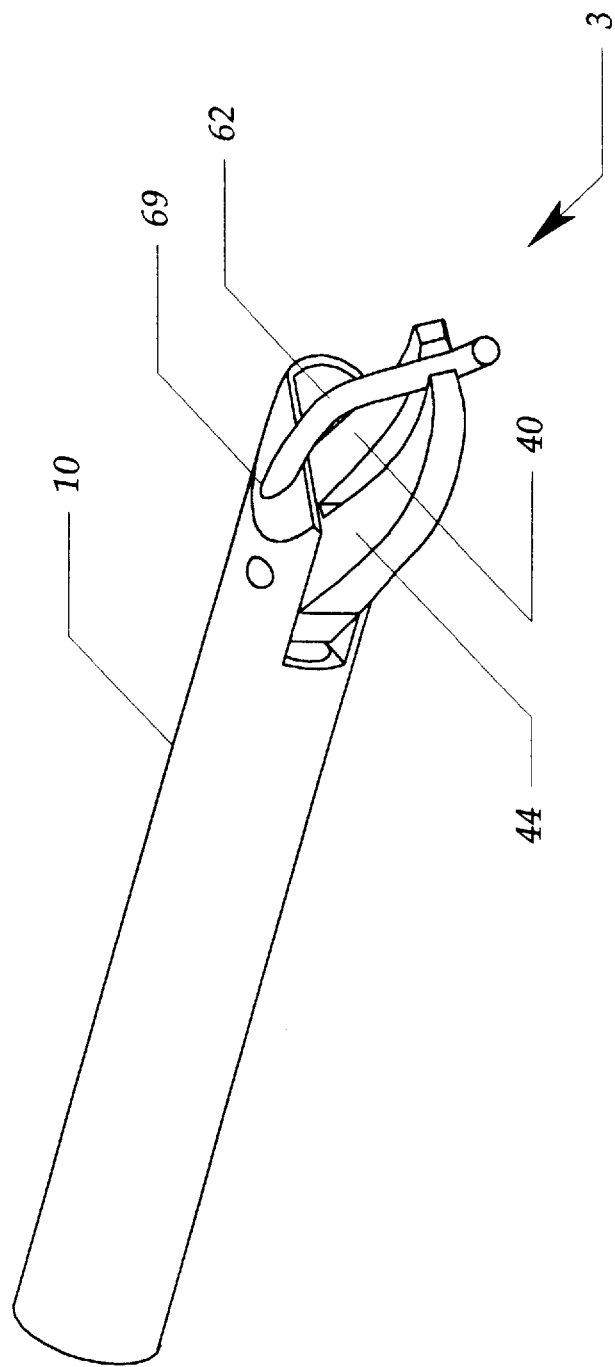
FIG. 9 is an isometric view of a portion of a surgical instrument, showing an endoscope extending from a lumen port and grasped by an end effector.
Figure 10:
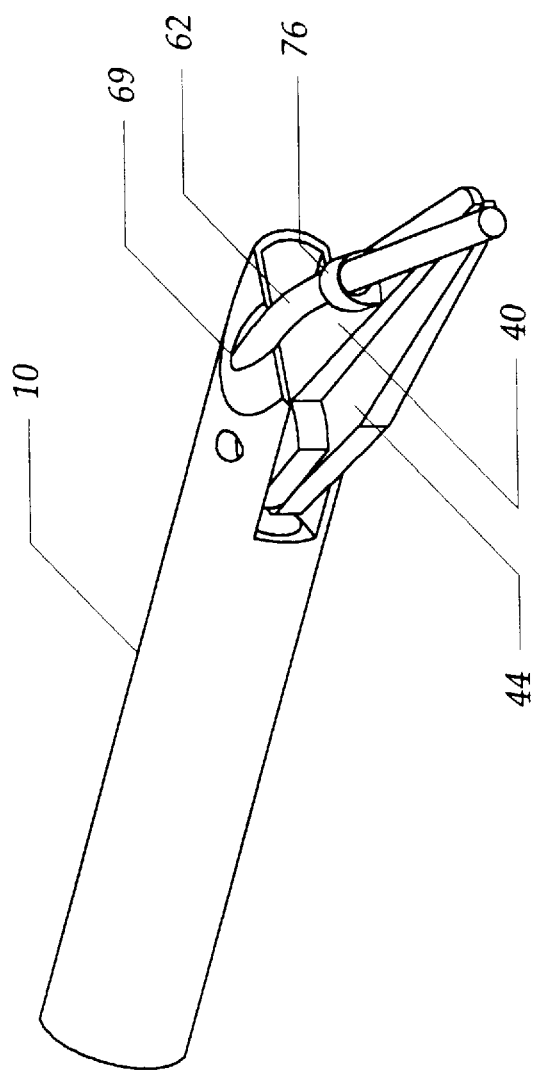
FIG. 10 is similar to the portion of the instrument shown in FIG. 9, but having an alternative end effector design.

FIGS. 9–11 show three different embodiments of an aspect of the invention where the end effector 3 in association with multiple lumens 66, 68 is used to position a fiber-optic catheter, such as fiber-optic scope 62, in a wide variety of orientations.

In the first scope/end effector embodiment, shown in FIG. 9, the scope 62 is fed through one of the side lumens 68 (see FIG. 8) and exits the tubular barrel 10 at an exit port 69 disposed on one side of the end effector 3. The end effector pieces 40 and 44 are curved dissector jaws instead of scissor blades. The dissector jaws 40 and 44 both curve toward the side of the end effector 3 on which the exit port 69 is disposed, making it possible to grasp with the dissector jaws 40 and 44 a scope 62 protruding from the exit port 69. After grasping the scope 62 with the dissector jaws 40 and 44, the surgeon is able to manipulate the end effector 3 to direct the scope 62 in various directions. To minimize the potential for damaging the end of the scope 62 with the end effector 3, the jaws 40 and 44 may be relieved or scalloped away (not shown), providing a place in which to receive the scope 62.

A second scope/end effector embodiment, shown in FIG. 10, also uses a scope 62 that is threaded through one of the side lumens 68 and which extends out of the exit port 69. In this embodiment, the end effector 3 has a loop (i.e., a bale) 76 on the end effector piece 40 that is adjacent the exit port 69. When the scope 62 is pushed through the lumen 68 and the end effector piece 40 is in a longitudinally extended position, it is possible to thread the scope 62 through the loop 76. Then, when the end effector blades 40 and 44 are pivoted, the scope 62 is bent in a large diameter arc so as to provide a view in a direction ranging from parallel to the longitudinal axis of the tubular barrel 10 to perpendicular to the longitudinal axis of the tubular barrel 10. Thus, in effect, the surgical instrument 1, having this scope/end effector configuration, also functions as an articulating scope.

Figure 11A:
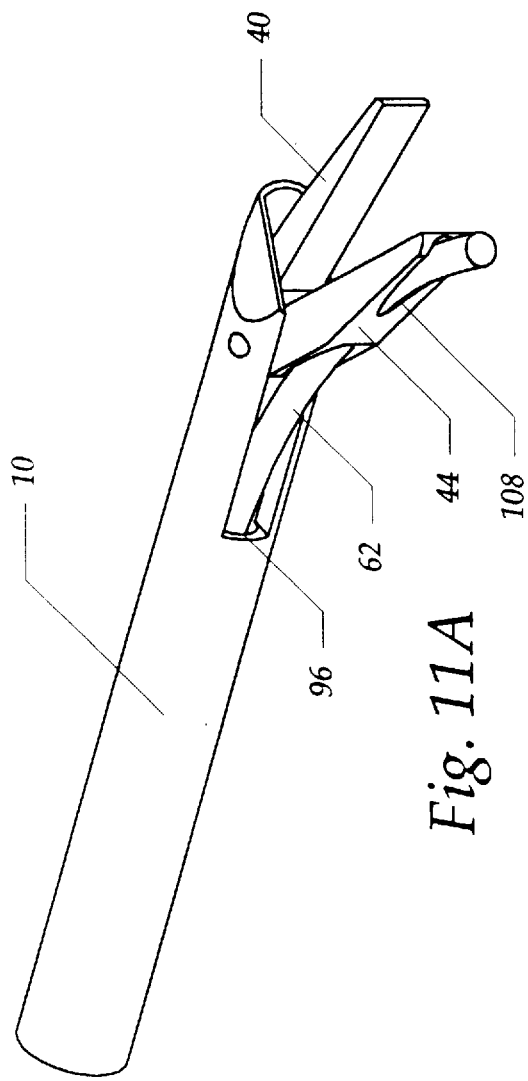
FIG. 11A is similar to the portion of the instrument shown in FIG. 9, but having an alternative end effector/lumen/lumen port embodiment, and showing one end effector piece slightly pivoted.
Figure 11B:
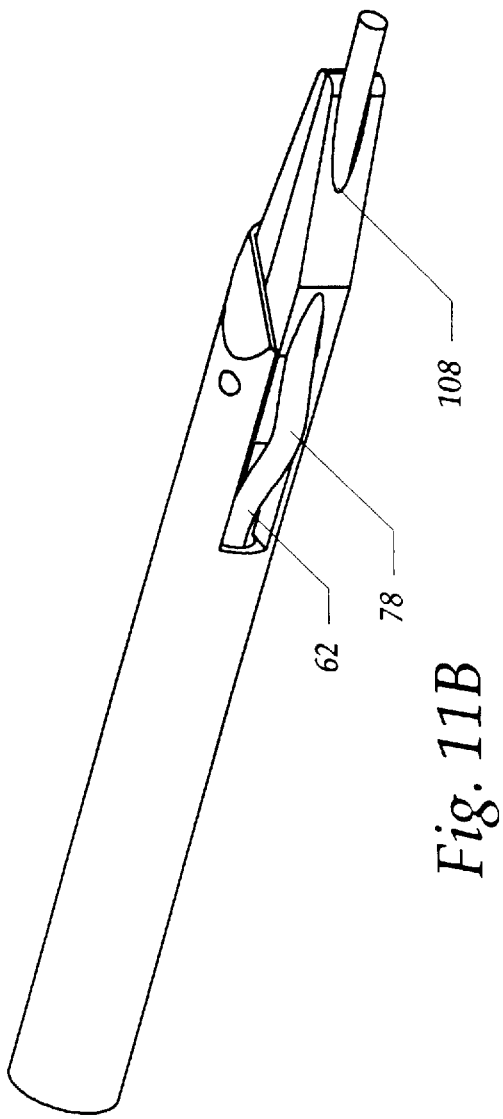
FIG. 11B is similar to FIG. 11A, but showing both end effector pieces longitudinally extended.

FIGS. 11A–B show a third scope/end effector embodiment. In this embodiment, the scope 62 is fed through the larger, central lumen 66 (see FIG. 8) and exits the tubular barrel 10 at an exit port 96 located immediately proximal of the end effector 3. The scope 62 may be larger in this embodiment, owing to the larger lumen 66. The end effector pieces 40 and 44 are "duck-bill"-type grasper jaws. End effector piece 44 has a channel 108 extending through much of its length. When the scope 62 is pushed through the lumen 66 and the end effector piece 44 is slightly pivoted from the longitudinally extended position, it is possible to thread the scope 62 through the channel 108 of end effector piece 44. Once the scope 62 is inserted, the end effector piece 44 may be extended longitudinally or pivoted 110° therefrom, thus functioning as an articulating scope. Note that in the longitudinally extended position, shown in FIG. 11B, the scope 62 protrudes slightly at reference numeral 78, because of the gear teeth 42 and 46 (see FIG. 2B and 2C).

Now referring to FIG. 12, the second application for multiple lumens 66, 68 will be described. In this application, the two side lumens 68 are used to supply irrigation fluid, and the central lumen 66 is for suction. Although the lumens 66 and 68 in this embodiment are irregular in cross-section, their cross-section could be circular, trapezoidal or any other suitable shape. A stream of water carried through the irrigation lumens 68 would be sprayed out of exit ports 69 (only one of which is shown also in FIG. 12) at the distal end of the tubular barrel 10, the exit ports 69 being on opposite sides of the end effector 3.

Figure 12:
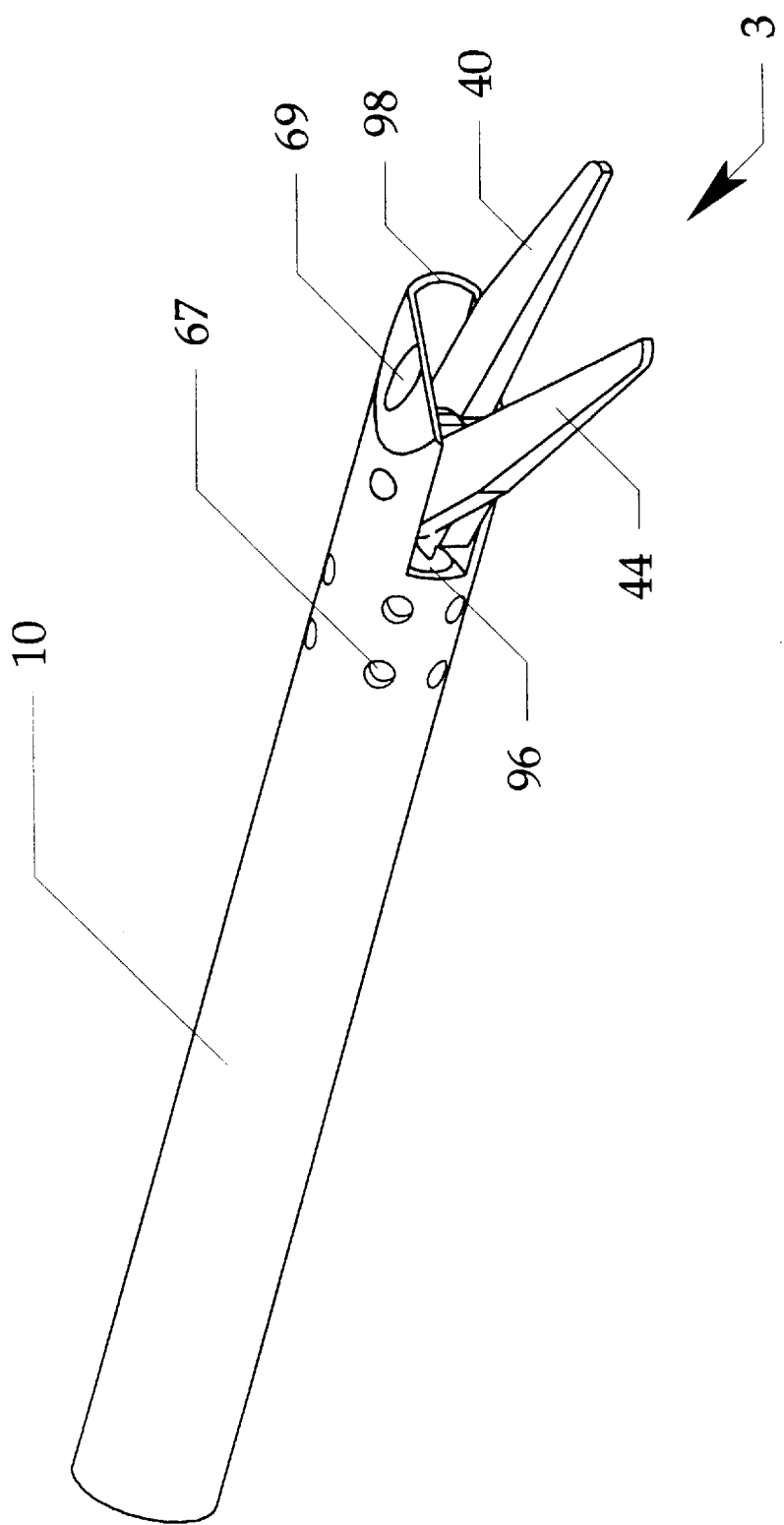
FIG. 12 is an isometric view of a portion of an instrument incorporating the lumen configuration shown in FIG. 8.

A suction port 96 leading to central lumen 66 is also located at the distal end of the tubular barrel 10, and is disposed immediately proximal of the end effector 3, as shown in FIG. 12. For suction, the end effector pieces 40 and 44 may be pivoted to their fullest extent and a distal tip 98 of the tubular barrel 10 positioned into pools of fluid to be aspirated. Aspiration performance may also be improved by drilling several small holes 67 between the suction lumen 66 and irrigation lumens 68, or through the tubular barrel 10 as shown. This configuration would allow all of the lumens 66, 68 to be used as suction or irrigation ports.

Figure 13:
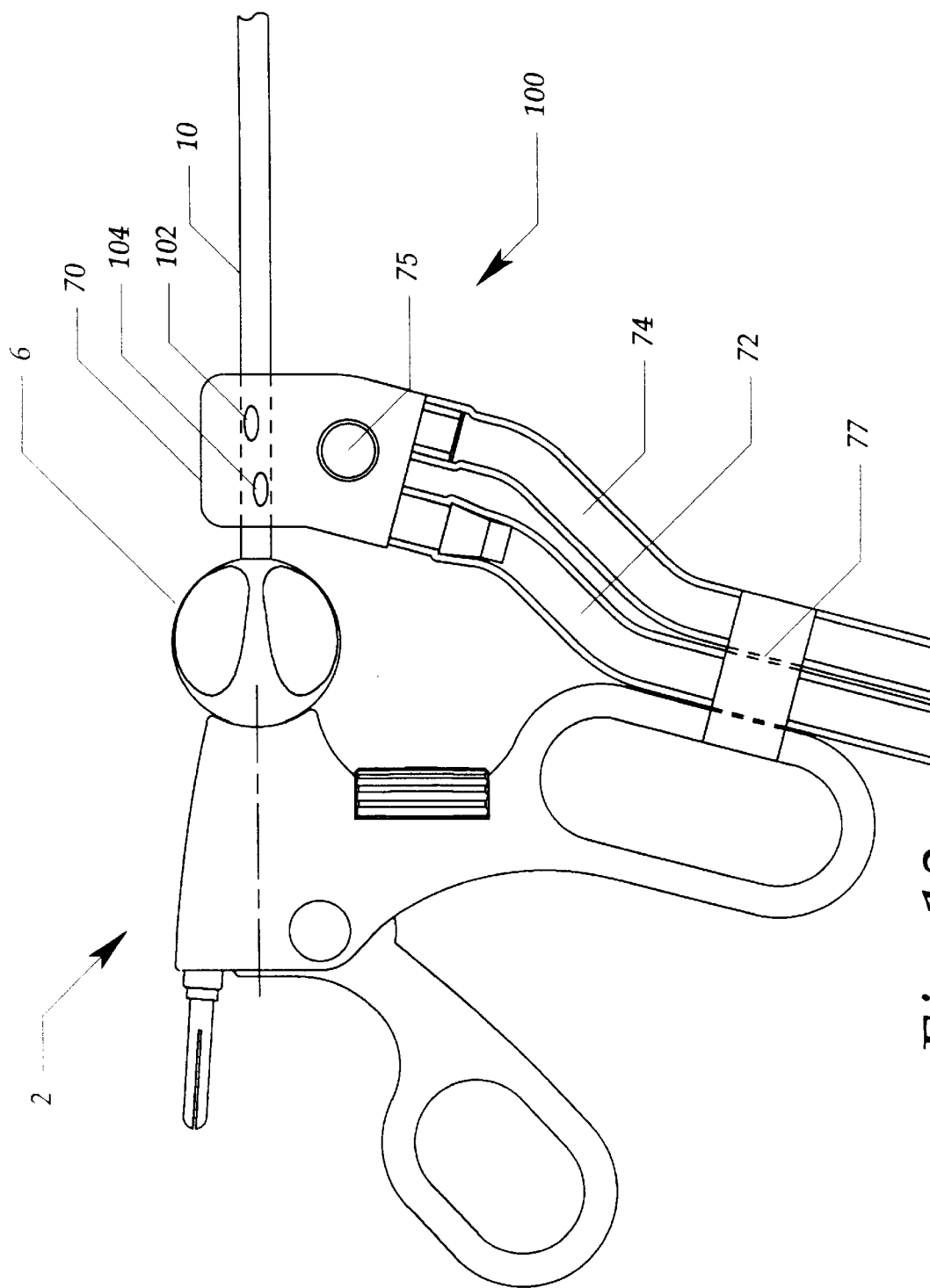
FIG. 13 is a side elevational view of a handle portion of an instrument in accordance with the invention, showing an optional suction/irrigation adapter.

FIG. 13 shows a suction-irrigation device 100 connected to the tubular barrel 10. The suction-irrigation device 100 includes an adaptor 70 that slides over the tubular barrel 10. The adaptor 70 seals around a proximal suction port 102 and a proximal irrigation supply port 104, the ports 102 and 104 being shown in dashed lines. A hose 72 for supplying irrigation solution and a hose 74 for supplying vacuum are both connected to the adaptor 70, as well as to the respective port 102 and 104 of each. A pushbutton 75 shown on the device is for regulating control valves for suction and irrigation. Alternatively, suction and irrigation may be controlled by buttons on the hose bundle (neither of which is shown). A clip or band 77 attaches the hoses 72 and 74 to the instrument handle 2 and prevents the device 100 from rotating or moving on the tubular barrel 10.

Figure 14:
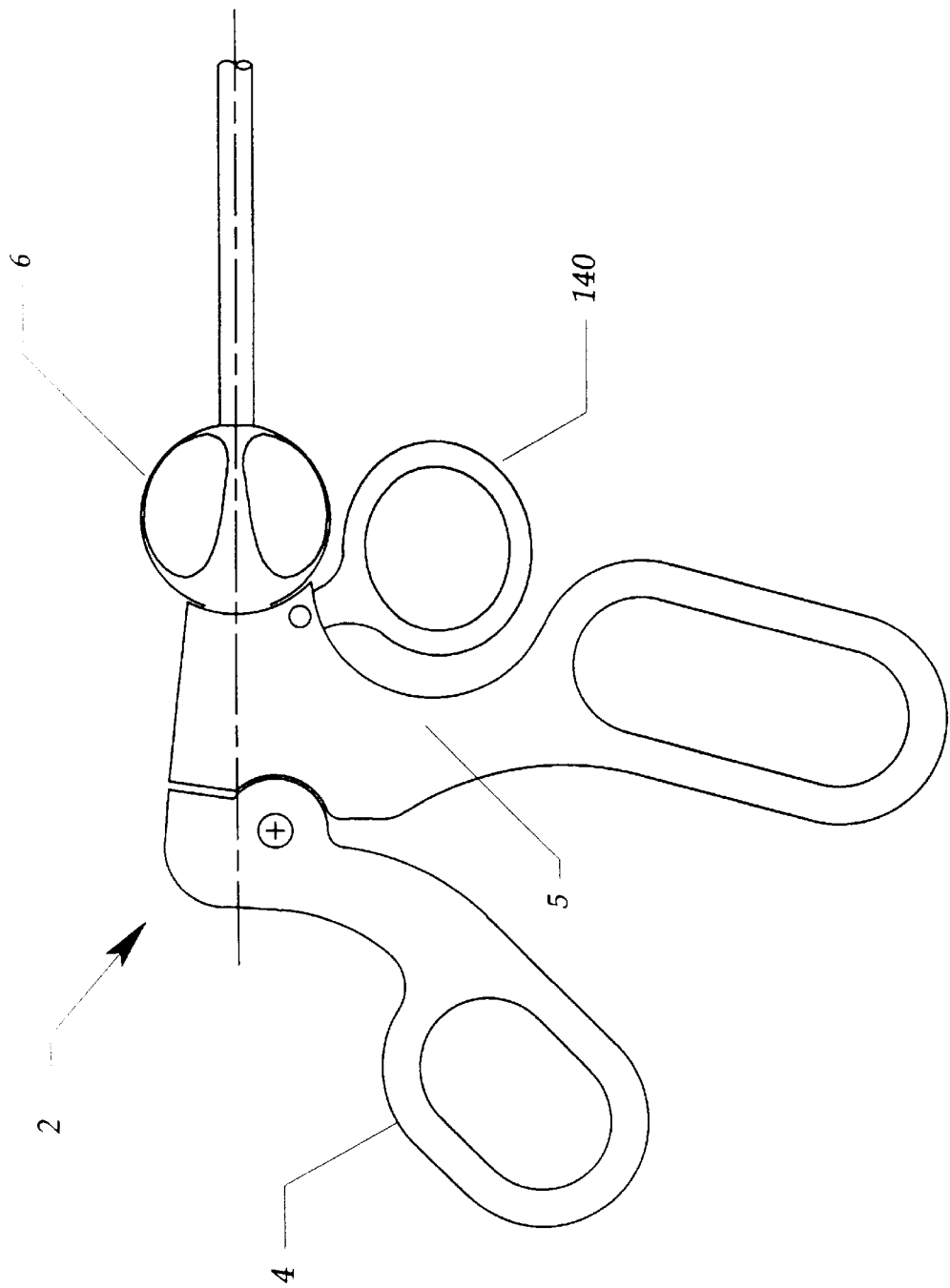
FIG. 14 is a side elevational view of a portion of an instrument similar to that shown in FIG. 1, but having an alternative pivot control design.

FIG. 14 shows an alternative embodiment of the handle 2 shown in FIG. 1. Instead of a fingerwheel roller, this handle has a second trigger 140 for pivoting both end effector pieces 40 and 44. The second trigger 140 pivots on an axis normal to the longitudinal axis of the tubular barrel 10. This pivoting of the second trigger 140 causes the barrel hub 26 (not shown) to be translated via a force multiplying linkage or rack and gear mechanism as discussed above. Alternatively, the trigger 140 may pivot around an axis either parallel to the axis of the tubular barrel 10 or at another angle. In this embodiment, the trigger 140 movement resembles a "flapping" motion rather than a traditional trigger "pivoting." This movement is easily achieved with the index finger as with the other embodiments described above.

Although the surgical instrument of the subject invention has been described with respect to preferred embodiments, it is apparent that changes may be made to the invention without departing from the spirit and scope of the invention as defined by the following claims.

What is claimed is:

1. A surgical instrument for use in endoscopy comprising:
   a tubular barrel with no joints and having a proximal end and a distal end;
   an end effector comprising a first working piece and a second working piece, each working piece being pivotally attached directly to the distal end of the tubular barrel, the two working pieces forming an operating angle therebetween;
   a handle attached to the proximal end of the tubular barrel, the handle comprising:
      an elongated stationary portion permanently fixed in alignment with the longitudinal axis of the tubular barrel, the stationary portion having a grip portion that is grippable by a single hand, wherein the stationary portion has a longitudinal axis that extends at an angle relative to the longitudinal axis of the tubular barrel;
      a manually operated actuating control; and
      a manually operated pivot control, the actuating and pivot controls being operable by the same hand which grips the grip portion; and
   linkage extending through the tubular barrel, the linkage operably connecting the actuating control and the pivot control to the first and second end effector working pieces, wherein
      in response to the actuating control being operated, the linkage acts on the end effector to alter the operating angle; and
      in response to the pivot control being operated, the linkage acts upon both the first and second end effector working pieces to pivot the end effector working pieces simultaneously and in the same direction while maintaining a substantially constant operating angle.

2. The surgical instrument according to claim 1, wherein the actuating control comprises a trigger lever, wherein movement of the trigger lever in a first direction decreases the operating angle between the first and second end effector pieces and movement of the trigger lever in an opposite direction increases the operating angle between the first and second end effector pieces.

3. The surgical instrument according to claim 2, wherein:
   the grip portion of the handle is designed to be gripped by at least a middle finger; and
   the trigger lever is designed to be operated by a thumb.

4. The surgical instrument according to claim 3, wherein:
   the grip portion comprises a finger loop for receiving at least a middle finger; and
   the trigger lever comprises a thumb loop for receiving a thumb.

5. The surgical instrument according to claim 3, wherein the pivot control is operated by an index finger.

6. The surgical instrument according to claim 5, wherein the pivot control is a fingerwheel roller disposed on the stationary portion of the handle, wherein rotation of the fingerwheel roller in a first direction pivots the first and second end effector pieces away from a longitudinally extended position and rotation of the fingerwheel roller in an opposite direction pivots the first and second end effector pieces toward the longitudinally extended position.

7. The surgical instrument according to claim 5, wherein the pivot control is a second lever attached to the stationary portion of the handle, wherein pivoting the second lever in a first direction pivots the first and second end effector pieces away from a longitudinally extended position and pivoting the second lever in an opposite direction pivots the first and second end effector pieces toward the longitudinally extended position.

8. The surgical instrument according to claim 7, wherein the second lever has a pivot axis that is approximately orthogonal to a longitudinal axis of the tubular barrel.

9. The surgical instrument according to claim 8, wherein the second lever comprises a finger loop for receiving an index finger for operating the second lever.

10. The surgical instrument according to claim 7, wherein the second lever has a pivot axis that is approximately parallel to a longitudinal axis of the tubular barrel.

11. The surgical instrument according to claim 10, wherein the second lever comprises a finger loop for receiving an index finger for operating the second lever.

12. The surgical instrument according to claim 5, wherein the handle further comprises a manually operated rotate control for rotating the tubular barrel and attached end effector, the rotate control being independent of the actuating control and the pivot control and further being operable by the same index finger that operates the pivot control.

13. The surgical instrument according to claim 12, wherein the rotate control comprises a rotatable knob, the knob being rotatably affixed to the tubular barrel so that it rotates with the knob.

14. The surgical instrument according to claim 12, wherein the handle further comprises a manually operated means for locking the trigger lever to prevent it from moving in the direction which increases the operating angle between the first and second end effector pieces, the locking means designed to be operated by the same index finger that operates the pivot control.

15. The surgical instrument according to claim 14, wherein the locking means comprises:
   a lock-and-release lever associated with the handle, the lock-and-release lever being manually pivotable into a locked position and a released position;

a ratchet bar disposed partially within the handle and pivotable about a pin, the ratchet bar having a first arm operably connected to the lock-and-release lever and a second arm having at its distal end a rack for engaging a mating catch attached to the trigger lever; and a spring for biasing the ratchet bar in a pivotal direction such that the rack of the second arm is biased toward the mating catch of the trigger lever, wherein, when the lock-and-release lever is in the released position the lock-and-release lever biases the ratchet bar in a pivotal direction against the bias of the spring and holds the rack of the second arm away from the mating catch, and when the lock-and-release lever is in the locked position the lever does not bias the ratchet bar and the bias of the spring causes the rack of the second arm to engage the mating catch of the trigger lever.

16. The surgical instrument according to claim 5, wherein the handle further comprises a manually operated means for locking the trigger lever to prevent it from moving in the direction which increases the operating angle between the first and second end effector pieces, the locking means designed to be operated by the same index finger that operates the pivot control.

17. The surgical instrument according to claim 16, wherein the locking means comprises:

a lock-and-release lever associated with the handle, the lock-and-release lever being manually pivotable into a locked position and a released position;

a ratchet bar disposed partially within the handle and pivotable about a pin, the ratchet bar having a first arm operably connected to the lock-and-release lever and a second arm having at its distal end a rack for engaging a mating catch attached to the trigger lever; and a spring for biasing the ratchet bar in a pivotal direction such that the rack of the second arm is biased toward the mating catch of the trigger lever, wherein, when the lock-and-release lever is in the released position the lock-and-release lever biases the ratchet bar in a pivotal direction against the bias of the spring and holds the rack of the second arm away from the mating catch, and when the lock-and-release lever is in the locked position the lever does not bias the ratchet bar and the bias of the spring causes the rack of the second arm to engage the mating catch of the trigger lever.

18. The surgical instrument according to claim 2, wherein the handle further comprises a manually operated means for locking the trigger lever to prevent it from moving in the direction which increases the operating angle between the first and second end effector pieces.

19. The surgical instrument according to claim 18, wherein the locking means is designed to be operated by the same hand that grips the grip portion of the handle.

20. The surgical instrument according to claim 19, wherein the locking means comprises:

a lock-and-release lever associated with the handle, the lock-and-release lever being manually pivotable into a locked position and a released position;

a ratchet bar disposed partially within the handle and pivotable about a pin, the ratchet bar having a first arm operably connected to the lock-and-release lever and a second arm having at its distal end a rack for engaging a mating catch attached to the trigger lever; and a spring for biasing the ratchet bar in a pivotal direction such that the rack of the second arm is biased toward the mating catch of the trigger lever, wherein, when the lock-and-release lever is in the released position the lock-and-release lever biases the ratchet bar in a pivotal direction against the bias of the spring and holds the rack of the second arm away from the mating catch, and when the lock-and-release lever is in the locked position the lever does not bias the ratchet bar and the bias of the spring causes the rack of the second arm to engage the mating catch of the trigger lever.

21. The surgical instrument according to claim 1, wherein the pivot control is a fingerwheel roller disposed on the stationary portion of the handle, wherein rotation of the fingerwheel roller in a first direction pivots the first and second end effector pieces away from a longitudinally extended position and rotation of the fingerwheel roller in an opposite direction pivots the first and second end effector pieces toward the longitudinally extended position.

22. The surgical instrument according to claim 21, wherein the fingerwheel roller includes a spring and detent mechanism for providing tactile feedback of the fingerwheel roller being rotated.

23. The surgical instrument according to claim 21, wherein the fingerwheel roller has an axis of rotation approximately orthoganol to a longitudinal axis of the tubular barrel.

24. The surgical instrument according to claim 1, wherein the handle further comprises a manually operated rotate control for rotating the tubular barrel and attached end effector, the rotate control being independent of the actuating control and the pivot control and further being operable by the same hand which grips the grip portion of the handle.

25. The surgical instrument according to claim 24 wherein the rotate control comprises a rotatable knob, the knob being rotatably affixed to the tubular barrel so that it rotates with the knob.

26. The surgical instrument according to claim 25, wherein the rotatable knob includes a spring and detent mechanism for providing tactile feedback of the rotatable knob being rotated.

27. The surgical instrument according to claim 24, wherein:

the grip portion of the handle is designed to be gripped by at least a middle finger;

the actuating control comprises a trigger lever designed to be operated by a thumb;

the pivot control is designed to be operated by an index finger; and the rotate control is designed to be operated by the same index finger that operates the pivot control.

28. The surgical instrument according to claim 27, wherein:

the grip portion of the handle comprises a finger loop for receiving at least a middle finger;

the actuating control comprises a thumb loop for receiving a thumb;

the pivot control comprises a fingerwheel roller disposed on the stationary portion of the handle, wherein rotation of the fingerwheel roller by the index finger in a first direction pivots the first and second end effector pieces away from a longitudinally extended position and rotation of the fingerwheel roller by the index finger in an opposite direction pivots the first and second end effector pieces toward the longitudinally extended position; and the rotate control comprises a rotatable knob, the knob being rotatably affixed to the tubular barrel so that it rotates with the knob.

29. The surgical instrument according to claim 24, wherein the pivot control further comprises a mechanical force multiplier operably connecting the force of rotation from the fingerwheel roller to the translation of the tubular barrel.

30. The surgical instrument according to claim 29, wherein the mechanical force multiplier comprises gears and pinions.

31. The surgical instrument according to claim 30, wherein the proximal portion of the tubular barrel further comprises a cylindrical rack, the cylindrical rack operably coupled to the gears and pinions of the force multiplier such that rotation of the fingerwheel roller causes a force to be applied to the cylindrical rack resulting in axial translation of the tubular barrel, while rotation of the tubular barrel by the rotate control does not cause axial translation of the tubular barrel.

32. The surgical instrument according to claim 1, wherein:
   the handle further comprises a plug for connecting the surgical instrument to a source of electrical current;
   the handle further comprises an electrically conductive path connecting the plug to the linkage extending through the tubular barrel;
   the linkage and the end effector are made from electrically conductive material, wherein electrical current is provided to an area of interest near the end effector.

33. The surgical instrument according to claim 32, wherein the tubular barrel is not electrically conductive.

34. A surgical instrument for use in endoscopy comprising:
   a tubular barrel having a proximal end and a distal end;
   an end effector comprising a first working piece and a second working piece, each piece being pivotally attached directly to the distal end of the tubular barrel, the two end effector pieces forming an operating angle therebetween;
   a linkage extending through the tubular barrel, the linkage comprising:
      a first elongated member operably connected to the first end effector working piece so that relative translational movement between the first elongated member and the tubular barrel causes the first end effector working piece to pivot; and
      a second elongated member operably connected to the second end effector working piece so that relative translational movement between the second elongated member and the tubular barrel causes the second end effector working piece to pivot; and
   a handle attached to the proximal end of the tubular barrel, the handle comprising:
      an elongated stationary piece permanently fixed in alignment with the longitudinal axis of the tubular barrel, the stationary portion having a grip portion that is grippable by a single hand, wherein the stationary piece has a longitudinal axis that extends at an angle relative to the longitudinal axis of the tubular barrel;
      a manually operated actuation control for causing relative translational movement between the first elongated member and the tubular barrel, thereby causing the first end effector working piece to pivot thereby effecting a change in the operating angle; and
      a manually operated pivot control for causing relative translational movement between the tubular barrel and both the first and second elongated members without significant relative translational movement between the first and second elongated members, thereby causing the first and second end effector pieces to pivot simultaneously and in the same direction while maintaining a substantially constant operating angle, the actuation and pivot controls being operable by the same hand which grips the grip portion of the handle.

35. The surgical instrument according to claim 34, wherein the actuating control comprises a trigger lever operably connected to the first elongated member and pivotable relative to the stationary piece of the handle, wherein pivotal movement of the trigger lever in a first pivotal direction translates the first elongated member in a first translational direction thus pivoting the first end effector working piece to decrease the operating angle, and wherein pivotal movement of the trigger lever in an opposite pivotal direction translates the first elongated member in a direction opposite the first translational direction thus pivoting the first end effector working piece to increase the operating angle.

36. The surgical instrument according to claim 34, wherein:
   the tubular barrel is axially translatable along its longitudinal axis and relative to the stationary piece of the handle; and
   the pivot control translates the tubular barrel relative to the stationary piece of the handle while the first and second elongated members are held translationally stationary relative to the stationary piece of the handle, thereby achieving the relative translational movement between the tubular barrel and both the first and second elongated members without significant relative translational movement between the first and second elongated members.

37. The surgical instrument according to claim 36, wherein the pivot control comprises a fingerwheel roller disposed on the stationary piece of the handle and operably connected to the tubular barrel, wherein rotation of the fingerwheel roller in a first rotational direction translates the tubular barrel relative to the handle in a first translational direction thus pivoting the end effector working pieces away from a longitudinally extended position, and wherein rotation of the fingerwheel roller in an opposite rotational direction translates the tubular barrel relative to the handle in a direction opposite the first translational direction thus pivoting the end effector working pieces toward the longitudinally extended position.

38. The surgical instrument according to claim 37, wherein the pivot control further comprises a mechanical force multiplier operably connecting the force of rotation from the fingerwheel roller to the translation of the tubular barrel.

39. The surgical instrument according to claim 38, wherein the mechanical force multiplier comprises gears and pinions.

40. The surgical instrument according to claim 39, wherein the proximal portion of the tubular barrel further comprises a cylindrical rack, the cylindrical rack operably coupled to the gears and pinions of the force multiplier such that rotation of the fingerwheel roller causes a force to be applied to the cylindrical rack resulting in translation of the tubular barrel.

41. The surgical instrument according to claim 37, wherein the fingerwheel roller has an axis of rotation approximately orthoganol to the longitudinal axis of the tubular barrel.

42. The surgical instrument according to claim 36, wherein the pivot control is a pivot control lever attached to the stationary piece of the handle and operably connected to the tubular barrel, wherein pivoting the pivot control lever in a first pivotal direction translates the tubular barrel relative to the handle in a first translational direction thus pivoting the end effector working pieces away from a longitudinally extended position, and wherein pivoting the pivot control lever in an opposite pivotal direction translates the tubular barrel relative to the handle in a direction opposite the first translational direction thus pivoting the end effector working pieces toward the longitudinally extended position.

43. The surgical instrument according to claim 42, wherein the pivot control lever comprises a finger loop for receiving an index finger for operating the pivot control lever, and wherein the pivot control lever has a pivot axis that is approximately normal to the longitudinal axis of the tubular barrel.

44. The surgical instrument according to claim 42, wherein the pivot control lever comprises a finger loop for receiving an index finger for operating the pivot control lever, and wherein the pivot control lever has a pivot axis that is approximately parallel to the longitudinal axis of the tubular barrel.

45. The surgical instrument according to claim 36, wherein:

the grip portion of the handle is designed to be gripped by at least a middle finger;

the actuating control comprises a thumb lever operably connected to the first elongated member and pivotable relative to the stationary piece of the handle, wherein pivotal movement of the thumb lever in a first pivotal direction translates the first elongated member in a first translational direction thus pivoting the first end effector working piece to decrease the operating angle, and wherein pivotal movement of the thumb lever in an opposite pivotal direction translates the first elongated member in a direction opposite the first translational direction thus pivoting the first end effector working piece to increase the operating angle;

the pivot control comprises a fingerwheel roller disposed on the stationary piece of the handle and operable by an index finger, the fingerwheel roller being operably connected to the tubular barrel, wherein rotation of the fingerwheel roller in a first rotational direction translates the tubular barrel relative to the handle in a first translational direction thus pivoting the end effector working pieces away from a longitudinally extended position, and wherein rotation of the fingerwheel roller in an opposite rotational direction translates the tubular barrel relative to the handle in a direction opposite the first translational direction thus pivoting the end effector working pieces toward the longitudinally extended position;

the handle further comprises a rotatable knob disposed around a proximal end of the tubular barrel and rotatable by the same index finger that operates the fingerwheel roller, the rotatable knob being rotatably affixed to the tubular barrel so that the tubular barrel and attached end effector rotate about a longitudinal axis of the tubular barrel as the knob is rotated.

46. The surgical instrument according to claim 45, wherein the handle further comprises a manually operated means for locking the thumb lever to prevent it from pivoting in the opposite pivotal direction to increase the operating angle.

47. The surgical instrument according to claim 46, wherein the locking means comprises:

a lock-and-release lever associated with the handle, the lock-and-release lever being manually pivotable into a locked position and a released position by the same index finger that operates the fingerwheel roller and the rotatable knob;

a ratchet bar pivotable about a pin connected to the stationary piece of the handle, the ratchet bar having a first arm operably connected to the lock-and-release lever and a second arm having at its distal end a rack for engaging a mating catch attached to the thumb lever; and a spring for biasing the ratchet bar in a pivotal direction such that the rack of the second arm is biased toward the mating catch of the thumb lever, wherein, when the lock-and-release lever is in the released position the lock-and-release lever biases the ratchet bar in a pivotal direction against the bias of the spring and holds the rack of the second arm away from the mating catch, and when the lock-and-release lever is in the locked position the lock-and-release lever does not bias the ratchet bar and the bias of the spring causes the rack of the second arm to engage the mating catch of the thumb lever, preventing it from pivoting in the opposite pivotal direction.

48. The surgical instrument according to claim 34, wherein the handle further comprises a manually operated rotate control for rotating the tubular barrel and attached end effector about a longitudinal axis of the tubular barrel, the rotate control being operable by the same hand which grips the grip portion of the handle.

49. The surgical instrument according to claim 48, wherein the rotate control comprises a rotatable knob disposed around a proximal end of the tubular barrel, the rotatable knob being rotatably affixed to the tubular barrel so that the tubular barrel and attached end effector rotate as the knob is rotated.

50. The surgical instrument according to claim 49, wherein:

the tubular barrel is axially translatable along its longitudinal axis and relative to the stationary piece of the handle;

the pivot control translates the tubular barrel relative to the stationary piece of the handle while the first and second elongated members are held translationally stationary relative to the stationary piece of the handle, thereby achieving the relative translational movement between the tubular barrel and both the first and second elongated members without significant relative translational movement between the first and second elongated members; and the rotatable knob is rotatably affixed to the tubular barrel by a pin extending internal of the rotatable knob and through a longitudinally extending slot in each side of the tubular barrel, the longitudinally extending slots in the tubular barrel allowing the tubular barrel to be translated axially relative to the stationary piece of the handle.

51. The surgical instrument according to claim 50, wherein:

the actuating control comprises a trigger lever pivotable relative to the stationary piece of the handle, the trigger lever being connected to the first elongated member by a ball-and-socket arrangement, wherein pivotal movement of the trigger lever in a first pivotal direction translates the first elongated member in a first translational direction thus pivoting the first end effector working piece to decrease the operating angle, and wherein pivotal movement of the trigger lever in an opposite pivotal direction translates the first elongated member in a direction opposite the first translational direction thus pivoting the first end effector working piece to increase the operating angle;

the first elongated member extending through the tubular barrel on one side of the pin extending through the tubular barrel, the pin forcing the first elongated member to be rotated inside the tubular barrel as the tubular barrel is rotated by the rotatable knob, the ball and socket connection between the first elongated member and the trigger lever permitting the rotational movement of the first elongated member despite the connection of the first elongated member to the trigger lever.

52. The surgical instrument according to claim 51, wherein the second elongated member is affixed at its proximal end to the pin extending through the tubular barrel thereby causing the first elongated member to be rotated with the tubular barrel as the tubular barrel is rotated by the rotatable knob and the first elongated member to be held translationally stationary relative to the stationary piece of the handle.

53. The surgical apparatus of claim 49, wherein the handle, actuation control, pivot control and rotate control are molded of plastic and are electrically non-conductive.

54. The surgical apparatus of claim 34, wherein the first and second elongated members are fabricated from lengths of shaped metallic wire.

* * * * *